(12) United States Patent
Reddy et al.

(10) Patent No.: US 9,102,664 B2
(45) Date of Patent: Aug. 11, 2015

(54) PROCESS FOR THE PREPARATION OF TRIAZOLE ANTIFUNGAL DRUG, ITS INTERMEDIATES AND POLYMORPHS THEREOF

(71) Applicant: MSN Laboratories Limited, Hyderabad, Andhra Pradesh (IN)

(72) Inventors: Manne Satyanarayana Reddy, Hyderabad (IN); Srinivasan Thirumalai Rajan, Hyderabad (IN); Sajja Eswaraiah, Hyderabad (IN); Sunkara Vishnuvardhan, Hyderabad (IN)

(73) Assignee: MSN Laboratories Private Limited, Medak District, Telangana (IN)

( * ) Notice: Subject to any disclaimer, the term of this patent is extended or adjusted under 35 U.S.C. 154(b) by 0 days.

(21) Appl. No.: 14/345,507

(22) PCT Filed: Sep. 17, 2012

(86) PCT No.: PCT/IN2012/000618
§ 371 (c)(1),
(2) Date: Mar. 18, 2014

(87) PCT Pub. No.: WO2013/042138
PCT Pub. Date: Mar. 28, 2013

(65) Prior Publication Data
US 2014/0343285 A1  Nov. 20, 2014

(30) Foreign Application Priority Data

Sep. 19, 2011 (IN) .......................... 3208/CHE/2011
Jan. 10, 2012 (IN) .............................. 98/CHE/2012
Feb. 7, 2012 (IN) ............................ 446/CHE/2012
May 29, 2012 (IN) .......................... 2154/CHE/2012

(51) Int. Cl.
| | | |
|---|---|---|
| C07D 405/14 | (2006.01) |
| C07D 413/06 | (2006.01) |
| C07D 263/24 | (2006.01) |
| C07D 307/24 | (2006.01) |
| C07C 67/08 | (2006.01) |
| C07C 67/31 | (2006.01) |
| C07C 67/60 | (2006.01) |
| C07C 211/27 | (2006.01) |
| C07C 241/04 | (2006.01) |
| C07C 251/76 | (2006.01) |
| C07C 51/09 | (2006.01) |
| C07C 51/487 | (2006.01) |
| C07C 59/66 | (2006.01) |
| C07D 263/26 | (2006.01) |

(52) U.S. Cl.
CPC .............. *C07D 405/14* (2013.01); *C07C 51/09* (2013.01); *C07C 51/487* (2013.01); *C07C 59/66* (2013.01); *C07C 67/08* (2013.01); *C07C 67/31* (2013.01); *C07C 67/60* (2013.01); *C07C 211/27* (2013.01); *C07C 241/04* (2013.01); *C07C 251/76* (2013.01); *C07D 263/24* (2013.01); *C07D 263/26* (2013.01); *C07D 307/24* (2013.01); *C07D 413/06* (2013.01); *C07B 2200/07* (2013.01)

(58) Field of Classification Search
USPC ......................................................... 544/366
See application file for complete search history.

(56) References Cited

U.S. PATENT DOCUMENTS

| | | |
|---|---|---|
| 5,403,937 A | 4/1995 | Saksena et al. |
| 5,625,064 A | 4/1997 | Andrews et al. |
| 5,661,151 A | 8/1997 | Saksena et al. |
| 6,713,481 B1 | 3/2004 | Andrews et al. |
| 6,958,337 B2 | 10/2005 | Andrews et al. |

FOREIGN PATENT DOCUMENTS

| | | |
|---|---|---|
| CN | 101824009 | 9/2010 |
| WO | WO 99/18097 | 4/1999 |

OTHER PUBLICATIONS

International Search Report for International Application No. PCT/IN2012/000618 "Process for the Preparation of Triazole Antifungal Drug, Its Intermediates and Polymorphs Thereof", Date of mailing: Mar. 14, 2013.

Notification Concerning Transmittal of International Preliminary Report on Patentability for International Application No. PCT/IN2012/000618 "Process for the Preparation of Triazole Antifungal Drug, Its Intermediates and Polymorphs Thereof", Date of Issuance: Mar. 25, 2013.

Written Opinion of the International Searching Authority for International Application No. PCT/IN2012/000618 "Process for the Preparation of Triazole Antifungal Drug, Its Intermediates and Polymorphs Thereof", Date of mailing: Mar. 14, 2013.

*Primary Examiner* — Kristin Vajda
(74) *Attorney, Agent, or Firm* — Hamilton, Brook, Smith & Reynolds, P.C.

(57) ABSTRACT

A process for the preparation of 4-[4-[4-[4-[[(3R,5R)-5-(2,4-difluorophenyl)tetrahydro-5-(1H-1,2,4-triazol-1-ylmethyl)-3-furanyl]methoxy]phenyl]-1-piperazinyl]phenyl]-2-[(1S,2S)-1-ethyl-2-hydroxypropyl]-2,4-dihydro-3H-1,2,4-triazol-3-one compound of formula-1, its intermediates and polymorphs thereof. (I).

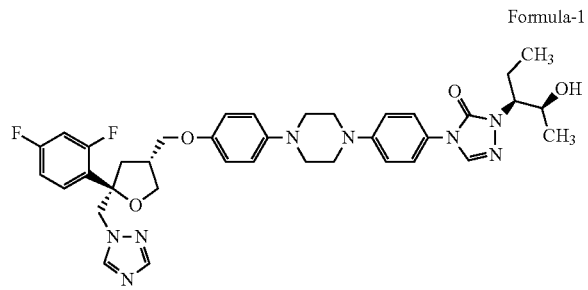

Formula-1

20 Claims, 4 Drawing Sheets

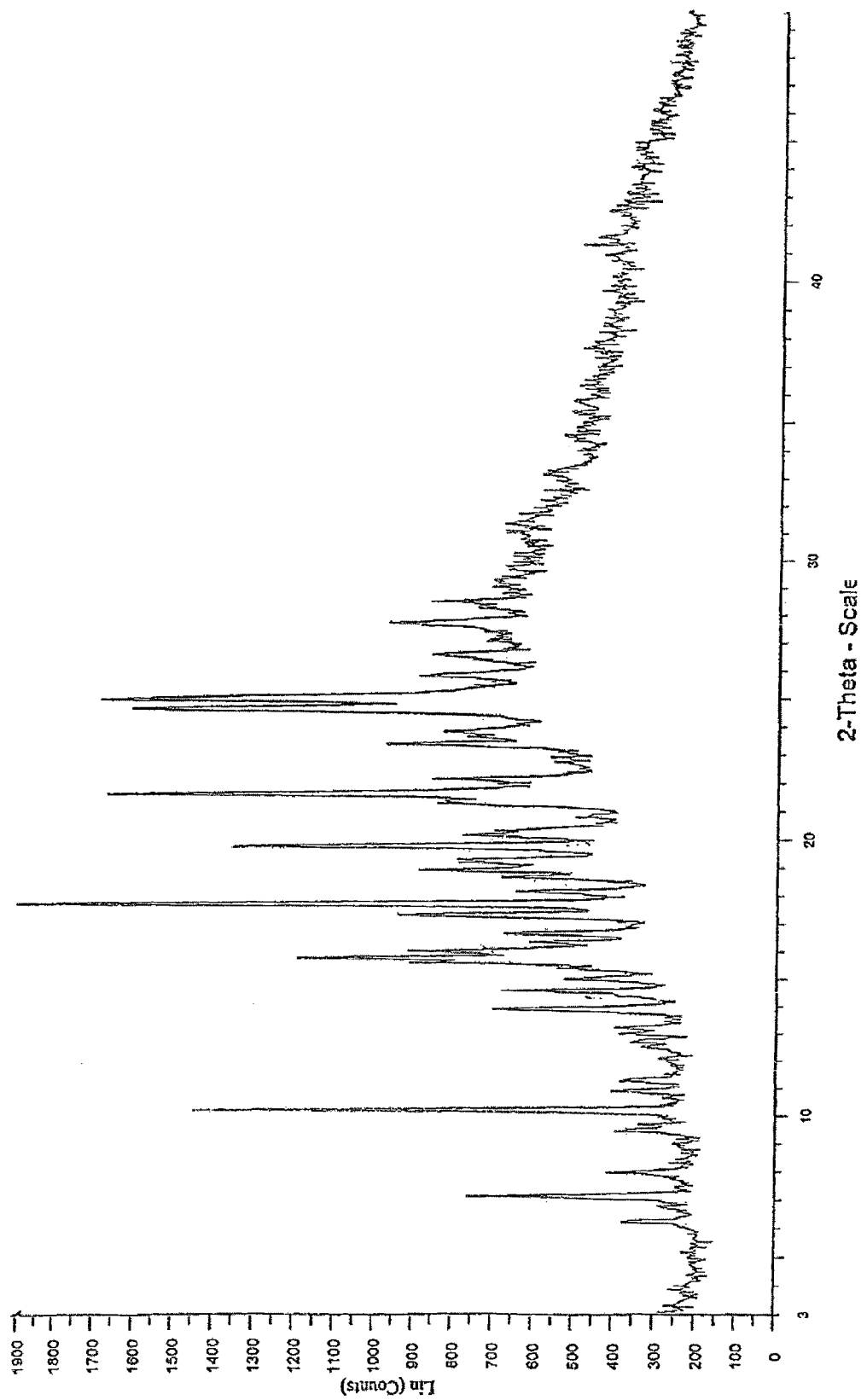

PROCESS FOR THE PREPARATION OF TRIAZOLE ANTIFUNGAL DRUG, ITS INTERMEDIATES AND POLYMORPHS THEREOF

RELATED APPLICATION

This application is the U.S. National Stage of International Application No. PCT/IN2012/000618, filed Sep. 17, 2012, which designates the U.S., published in English, and claims priority under 35 U.S.C. §§119 or 365(c) to Indian Patent Application No. 3208/CHE/2011, filed on Sep. 19, 2011, Indian Patent Application No. 98/CHE/2012, filed on Jan. 10, 2012, Indian Patent Application No. 446/CHE/2012 filed on Feb. 7, 2012 and Indian Patent Application No. 2154/CHE/2012, filed on May 29, 2012. The entire teachings of the above applications are incorporated herein by reference.

FIELD OF THE INVENTION

The present invention relates to a process for the preparation of ((3S,5R)-5-((1H-1,2,4-triazol-1-yl)methyl)-5-(2,4-difluorophenyl)tetrahydrofuran-3-yl)methyl-4-methyl benzenesulfonate compound of formula-10 useful in the preparation of Triazole Antifungal drug represented/by the following structural formula-1:

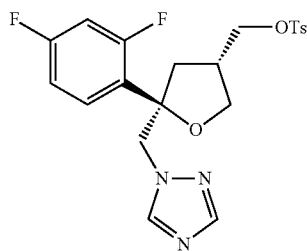

The present invention also relates to an improved process for the preparation of compound of formula-1 through novel intermediates.

Further, the present invention relates to novel crystalline forms of triazole antifungal drug and its intermediate compound and process for the preparation of said crystalline and amorphous form of compound of formula-1.

BACKGROUND OF THE INVENTION

The triazole antifungal drug i.e., 4-[4-[4-[4-[[(3R,5R)-5-(2,4-difluorophenyl) tetrahydro-5-(1H-1,2,4-triazol-1-ylmethyl)-3-furanyl]methoxy]phenyl]-1-piperazinyl]phenyl]-2-[(1S,2S)-1-ethyl-2-hydroxypropyl]-2,4-dihydro-3H-1,2,4-triazol-3-one is commonly known as posaconazole, an antifungal agent which is used against a wide range of fungal pathogens, including both yeast and molds.

U.S. Pat. No. 5,403,937 discloses a process for the preparation of key intermediate of posaconazole, specifically ((3S,5R)-5-((1H-1,2,4-triazol-1-yl)methyl)-5-(2,4-difluorophenyl)tetrahydrofuran-3-yl)methyl-4-methylbenzenesulfonate. The process involves the usage of n-butyllithium during the preparation of oxazolidinone lithium salt, which is extremely flammable. The process requires column chromatographic purification at different stages to purify the intermediates which is tedious and lengthy process. The above said drawbacks make the process unviable on commercial scale.

In view of the above, there is an obvious need to find an efficient and industrially advantageous process for the synthesis of above said key intermediate of posaconazole which overcomes the problems associated with the prior art such as prolonged reaction time, low yields and tedious purifications.

U.S. Pat. No. 5,661,151 (hereinafter referred to as "151") discloses several substituted tetrahydrofuran antifungal compounds, including posaconazole. This patent discloses several processes for the preparation of posaconazole.

According to one process, posaconazole is prepared by the condensation of toluene-4-sulfonic acid (−)-(5R-cis)-5-(2,4-difluorophenyl)-5-[1,2,4]triazol-1-ylmethyl tetrahydro-3-furanmethyl ester with N-protected triazolone derivative in the presence of a strong base in an aprotic solvent to give a compound, which is then deprotected using hydrochloric acid in methanol followed by N-alkylation with brosylated (2S, 3R) alcohol in the presence of cesium carbonate in an aprotic solvent to give hydroxy protected posaconazole, and is then deprotected to give posaconazole.

The major drawback of the above said process is that, the N-alkylation is carried out on cyclized triazolone intermediate which requires excess amount of an expensive alkylating agent, and results in a mixture of N-alkylated and O-alkylated posaconazole, necessitating laborious purification methods Formula-10

Formula-1

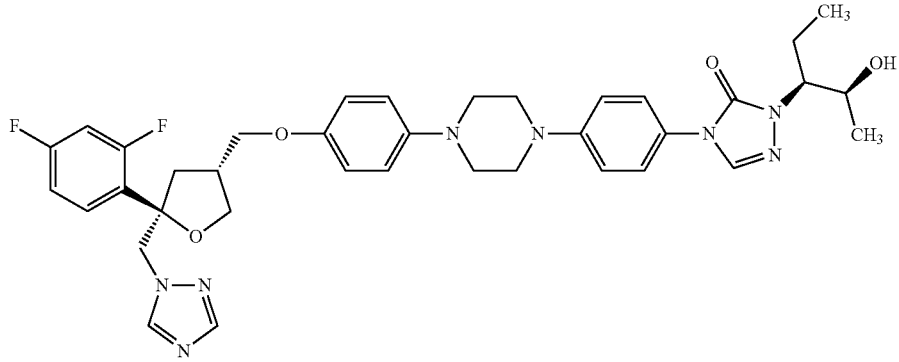

such as column chromatography which is a time consuming and tedious process, especially for large quantities hence it is not suitable for large scale production and further results in low yields of posaconazole.

U.S. Pat. No. 5,625,064 discloses a process for the preparation of posaconazole which involves the condensation of 1-((2S,3R)-2-(benzyloxy)pentan-3-yl)-4-(4-(4-(4-hydroxyphenyl)piperazin-1-yl)phenyl)-1H-1,2,4-triazol-5(4H)-one with (−)-(5R-cis)-5-(2,4-difluorophenyl)-5-[1,2,4]triazol-1-ylmethyl-tetrahydro-3-furanmethylester derivative in the presence of a base to give benzyl ether of posaconazole which is then deprotected either with palladium on carbon in the presence of formic acid or aqueous hydrobromic acid to form posaconazole.

The above process suffers from several drawbacks such as low yield. It was observed that condensation of unprotected hydroxyl derivative with hydrazine derivative results in low yield of the compound. Further, condensation of O-benzyl protected phenyl carbamate derivative results in the formation of impurities which requires tedious purification processes hence results in low yield. In addition, the deprotection of benzyl ether of posaconazole in the presence of formic acid does not go to completion of the reaction or requires more than 30-35 hours. This may lead to degradation of final product and may require tedious purification processes such as chromatography purification or refluxing of the product with aqueous sodium hydroxide solution for another 24 hours as reported in the prior art. On the other hand, deprotection of benzyl ether of posaconazole with aqueous hydrobromic acid results in the degradation of compound of formula 1 and also requires laborious purification methods to purify posaconazole, hence results in the loss of yield and purity.

In view of the above, there is an obvious need to find an efficient and industrially advantageous process for the synthesis of posaconazole which overcomes the problems associated with the prior art such as prolonged reaction time, use of hazardous reagents, stringent reaction conditions, low yields and tedious purifications.

Three polymorphic forms of posaconazole designated as forms I, II and III are described and characterized in WO 99/18097 (U.S. Pat. Nos. 6,713,481, 6,958,337). Crystalline forms II and III were found to be unstable under the conditions investigated, so that crystalline form I was considered to be useful in the development of a pharmaceutical product.

Amorphous form of posaconazole produced as per the process disclosed in U.S. Pat. No. 5,661,151 by using 6N HCl in methanol is not stable. As of the date, there is no process available in the art for the preparation of stable amorphous posaconazole.

Hence there is a need to develop an alternative process for the preparation of amorphous form of posaconazole, which is more stable when used in a pharmaceutical composition and/or which have properties that make them suitable for bulk preparation and handling.

In view of the foregoing, there is an obvious need to find an efficient and industrially advantageous process for the synthesis of posaconazole and its intermediates as well as novel polymorphic forms of said compounds, which overcomes the problems associated with the prior art such as prolonged reaction time, use of hazardous reagents, stringent reaction conditions, low yields and tedious purifications.

BRIEF DESCRIPTION OF THE INVENTION

The first aspect of the present invention is to provide an improved process for the preparation of (3S,5R)-5-(2,4-difluorophenyl)-5-(iodomethyl)tetrahydrofuran-3-carboxylic acid compound of formula-7, comprising of the following steps:
a) Reacting the 4-(2,4-difluorophenyl)pent-4-enoic acid compound of formula-2 with (R)-4-phenyloxazolidin-2-one compound of formula-3 in presence of activating agent and a suitable base in a suitable solvent to provide (R)-3-(4-(2,4-difluorophenyl)pent-4-enoyl)-4-phenyloxazolidin-2-one compound of formula-4,
b) hydroxy methylating the compound of formula-4 with 1,3,5-trioxane in the presence of a suitable base and suitable catalyst in a suitable solvent to provide (R)-3-((S)-4-(2,4-difluorophenyl)-2-(hydroxymethyl)pent-4-enoyl)-4-phenyl oxazolidin-2-one compound of formula-5,
c) cyclizing the compound of formula-5 in-situ in the presence of iodine and a suitable base in a suitable solvent to provide (R)-3-((3S,5R)-5-(2,4-difluorophenyl)-5-(iodomethyl)tetrahydrofuran-3-carbonyl)-4-phenyloxazolidin-2-one compound of formula-6,
d) hydrolyzing the compound of formula-6 with a suitable base in the presence of a suitable catalyst in a suitable solvent to provide (3S,5R)-5-(2,4-difluorophenyl)-5-(iodomethyl)tetrahydrofuran-3-carboxylic acid compound of formula-7.

The second aspect of the present invention is to provide a novel process for the preparation of (R)-3-((S)-4-(2,4-difluorophenyl)-2-(hydroxymethyl)pent-4-enoyl)-4-phenyloxazolidin-2-one compound of formula-5, comprising of:
a) Reacting 4-(2,4-difluorophenyl)pent-4-enoic acid compound of formula-2 with (R)-4-phenyloxazolidin-2-one compound of formula-3 in presence of a suitable activating agent and a suitable base in a suitable solvent to provide (R)-3-(4-(2,4-difluorophenyl)pent-4-enoyl)-4-phenyloxazolidin-2-one compound of formula-4,
b) hydroxy methylating the compound of formula-4 with 1,3,5-trioxane in the presence of a base and a suitable catalyst in a suitable solvent to provide (R)-3-((S)-4-(2,4-difluorophenyl)-2-(hydroxymethyl)pent-4-enoyl)-4-phenyloxazolidin-2-one compound of formula-5 as residue, which is optionally isolated as a solid from a suitable solvent.

The third aspect of the present invention is to provide a novel process for the preparation of ((3R,5R)-5-(2,4-difluorophenyl)-5-(iodomethyl)tetrahydrofuran-3-yl) methanol compound of formula-8, comprising of:
a) Hydrolyzing the (R)-3-((3S,5R)-5-(2,4-difluorophenyl)-5-(iodomethyl)tetrahydro furan-3-carbonyl)-4-phenyloxazolidin-2-one compound of formula-6 with a suitable base in the presence of suitable catalyst in a suitable solvent to provide (3S,5R)-5-(2,4-difluorophenyl)-5-(iodomethyl)tetrahydrofuran-3-carboxylic acid compound of formula-7,
b) reducing the compound of formula-7 with a suitable reducing agent in a suitable solvent to provide ((3R,5R)-5-(2,4-difluorophenyl)-5-(iodomethyl)tetrahydro furan-3-yl)methanol compound of formula-8.

The fourth aspect of the present invention is to provide an improved process for the preparation of ((3S,5R)-5-((1H-1,2,4-triazol-1-yl)methyl)-5-(2,4-difluorophenyl)tetra hydrofuran-3-yl)methyl-4-methylbenzenesulfonate compound of formula-10, comprising of the following steps:
a) Reacting the 4-(2,4-difluorophenyl)pent-4-enoic acid compound of formula-2 with (R)-4-phenyloxazolidin-2-one compound of formula-3 in the presence of a suitable activating agent and a suitable base in a suitable solvent to provide (R)-3-(4-(2,4-difluorophenyl)pent-4-enoyl)-4-phenyloxazolidin-2-one compound of formula-4, b) hydroxy methylating the compound of formula-4 with 1,3,5-trioxane in the presence of a suitable base and a suitable catalyst in a suitable solvent to provide (R)-3-((S)-4-(2,4-difluorophenyl)-2-(hydroxymethyl)pent-4-enoyl)-4-phenyl oxazolidin-2-one compound of formula-5, c) cyclizing the compound of formula-5 in-situ in the presence of iodine and a suitable base in a suitable solvent to provide (R)-3-((3S,5R)-5-(2,4-difluorophenyl)-5-(iodomethyl)tetrahydrofuran-3-carbonyl)-4-phenyloxazolidin-2-one compound of formula-6, d) hydrolyzing the compound of formula-6 in the presence of a suitable base and a catalyst in a suitable solvent to provide (3S,5R)-5-(2,4-difluorophenyl)-5-(iodomethyl)tetrahydrofuran-3-carboxylic acid compound of formula-7, e) reducing the compound of formula-7 with a suitable reducing agent in a suitable solvent to provide ((3R,5R)-5-(2,4-difluorophenyl)-5-(iodomethyl)tetrahydro furan-3-yl)methanol compound of formula-8, f) reacting the compound of formula-8 with 1H-1,2,4-triazole in the presence of a suitable base in a suitable solvent to provide ((3R,5R)-5-((1H-1,2,4-triazol-1-yl)methyl)-5-(2,4-difluorophenyl)tetrahydrofuran-3-yl) methanol compound of formula-9, g) reacting the compound of formula-9 in-situ with tosyl chloride in the presence of a suitable base in a suitable solvent to provide ((3S,5R)-5-((1H-1,2,4-triazol-1-yl)methyl)-5-(2,4-difluorophenyl)tetrahydrofuran-3-yl) methyl 4-methyl benzene sulfonate compound of formula-10.

The fifth aspect of the present invention is to provide novel intermediates which are useful in the preparation of triazole derivative compound of formula-1, comprising of the following steps:
a) (R)-3-(4-(2,4-difluorophenyl)pent-4-enoyl)-4-phenyloxazolidin-2-one compound of formula-4,
b) (R)-3-((S)-4-(2,4-difluorophenyl)-2-(hydroxymethyl) pent-4-enoyl)-4-phenyl oxazolidin-2-one compound of formula-5,
c) (R)-3-((3S,5R)-5-(2,4-difluorophenyl)-5-(iodomethyl) tetrahydrofuran-3-carbonyl)-4-phenyloxazolidin-2-one compound of formula-6,
d) (3S,5R)-5-(2,4-difluorophenyl)-5-(iodomethyl)tetrahydrofuran-3-carboxylic acid compound of formula-7.

The sixth aspect of the present invention is to provide an improved process for the preparation of (S)—N'-(2-(benzyloxy)propylidene)formohydrazide compound of formula-16, comprising of the following steps:
a) Reacting the racemic methyl lactate compound of formula-11 with benzyl chloride in the presence of a suitable base in a suitable solvent to provide methyl 2-(benzyloxy)propanoate compound of formula-12,
b) hydrolyzing the compound of formula-12 in-situ with a suitable base in a suitable solvent to provide 2-(benzyloxy)propanoic acid compound of formula-13,
c) resolving the compound of formula-13 in-situ with (S)-1-phenylethanamine in a suitable solvent to provide (S)-1-phenylethanamine salt of (S)-2-(benzyloxy) propanoic acid compound of formula-13 a,
d) reacting the compound of formula-13a with alcoholic solvent in presence of a suitable activating agent in a suitable solvent to provide (S)-methyl 2-(benzyloxy) propanoate compound of formula-14, e) reducing the compound of formula-14 with a suitable reducing agent in a suitable solvent to provide (S)-2-(benzyloxy)propanal compound of formula-15, f) reacting the compound of formula-15 in-situ with formyl hydrazine in a suitable solvent to provide (S)—N'-(2-(benzyloxy)propylidene)formylhydrazide compound of formula-16.

The seventh aspect of the present invention is to provide (S)-1-phenylethanamine salt of (S)-2-(benzyloxy)propanoic acid compound of formula-13a, a novel intermediate which is useful in the preparation of (S)—N'-(2-(benzyloxy)propylidene)formylhydrazide compound of formula-16.

The eighth aspect of the present invention is to provide an improved process for the preparation of phenyl 4-(4-(4-hydroxyphenyl)piperazin-1-yl)phenylcarbamate compound of formula-19, which comprising of reacting 4-(4-(4-aminophenyl)piperazin-1-yl)phenol compound of formula-18 with arylchloroformate in a suitable solvent.

The ninth aspect of the present invention is to provide an improved process for the preparation of pure Triazole derivative compound of formula-1, comprising of the following steps:
a) Reacting the (S)—N'-(2-(benzyloxy)propylidene) formylhydrazide compound of formula-16 with ethyl magnesium halide in presence of bis(trimethylsilyl) acetamide in a suitable solvent to provide N'-((2S,3S)-2-(benzyloxy)pentan-3-yl)formylhydrazide compound of formula-17,
b) reacting the compound of formula-17 in-situ with phenyl 4-(4-(4-hydroxyphenyl)piperazin-1-yl)phenylcarbamate compound of formula-19 in the presence of a base in a suitable solvent to provide 1-((2S,3S)-2-(benzyloxy) pentan-3-yl)-4-(4-(4-(4-hydroxyphenyl)piperazin-1-yl)phenyl)-1H-1,2,4-triazol-5(4H)-one compound of formula-20,
c) condensing the compound of formula-20 with ((3S,5R)-5-((1H-1,2,4-triazol-1-yl)methyl)-5-(2,4-difluorophenyl)tetrahydrofuran-3-yl)methyl-4-methylbenzene sulfonate compound of formula-10 in the presence of a base in a suitable solvent to provide 4-(4-(4-(4-(((3R,5R)-5-((1H-1,2,4-triazol-1-yl)methyl)-5-(2,4-difluoro phenyl) tetrahydrofuran-3-yl)methoxy)phenyl)piperazin-1-yl) phenyl)-1-((2S,3S)-2-(benzyloxy)pentan-3-yl)-1H-1,2,4-triazol-5(4H)-one compound of formula-21,
d) debenzylating the compound of formula-21 using Pd/C in the presence of mineral acid under hydrogen pressure in a suitable solvent to provide Triazole derivative compound of formula-1,
e) optionally purifying the compound obtained in step-(d) from a suitable solvent to provide pure compound of formula-1.

The tenth aspect of the present invention is to provide an improved process for the preparation of 4-(4-(4-(4-(((3R, 5R)-5-((1H-1,2,4-triazol-1-yl)methyl)-5-(2,4-difluoro phenyl)tetrahydrofuran-3-yl)methoxy)phenyl)piperazin-1-yl) phenyl)-1-((2S,3S)-2-(benzyloxy)pentan-3-yl)-1H-1,2,4-triazol-5(4H)-one compound of formula-21, comprising of condensing the 1-((2S,3S)-2-(benzyloxy)pentan-3-yl)-4-(4-(4-(4-hydroxy phenyl)piperazin-1-yl)phenyl)-1H-1,2,4-triazol-5(4H)-one compound of formula-20 with ((3S,5R)-5-((1H-1,2,4-triazol-1-yl)methyl)-5-(2,4-difluorophenyl) tetrahydrofuran-3-yl)methyl-4-methyl benzenesulfonate compound of formula-10 in the presence of a suitable base in a solvent to provide compound of formula-21.

The eleventh aspect of the present invention is to provide an improved process for the preparation of amorphous 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one compound of formula-21, comprising of condensing the 1-((2S,3S)-2-(benzyloxy)pentan-3-yl)-4-(4-(4-(4-hydroxy phenyl)piperazin-1-yl)phenyl)-1H-1,2,4-triazol-5(4H)-one compound of formula-20 with ((3S,5R)-5-((1H-1,2,4-triazol-1-yl)methyl)-5-(2,4-difluorophenyl)tetrahydrofuran-3-yl)methyl-4-methyl benzenesulfonate compound of formula-10 in the presence of a suitable base in a solvent to provide compound of formula-21, followed by quenching the reaction mixture with water and neutralizing the reaction mixture with acid to provide amorphous compound of formula-21.

The twelfth aspect of the present invention is to provide a novel process for the preparation of amorphous 4-[4-[4-[4-[[(3R,5R)-5-(2,4-difluoro phenyl)tetrahydro-5-(1H-1,2,4-triazol-1-ylmethyl)-3 furanyl]methoxy]phenyl]-1-piperazinyl]phenyl]-2-[(1S,2S)-1-ethyl-2-hydroxypropyl]-2,4-dihydro-3H-1,2,4-triazol-3-one compound of formula-1, which comprising of:
  a) Dissolving the compound of formula-1 in a suitable solvent,
  b) filtering the reaction mixture,
  c) adding the filtrate to a suitable non-polar anti-solvent,
  d) stirring the reaction mixture to obtain solid,
  e) filtering the solid and then drying to get amorphous form of compound of formula-1.

The thirteenth aspect of the present invention is to provide a one-pot process for the preparation of amorphous 4-[4-[4-[4-[[(3R,5R)-5-(2,4-difluoro phenyl)tetrahydro-5-(1H-1,2,4-triazol-1-ylmethyl)-3 furanyl]methoxy]phenyl]-1-piperazinyl]phenyl]-2-[(1S,2S)-1-ethyl-2-hydroxypropyl]-2,4-dihydro-3H-1,2,4-triazol-3-one compound of formula-1, which comprising of:
  a) Reacting the 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one with Pd/C under hydrogen pressure in the presence of mineral acid in a suitable solvent,
  b) filtering the reaction mixture and adding organic solvent to the filtrate,
  c) cooling the reaction mixture and adjusting the pH of the reaction mixture,
  d) adding water to the reaction mixture,
  e) filtering the precipitated solid,
  f) adding organic solvent to the solid, obtained in step-(e) and heating the reaction mixture,
  g) filtering the reaction mixture,
  h) adding water to the filtrate and stirring the reaction mixture,
  i) filtering the precipitated solid,
  j) optionally, purifying the obtained solid in step-(i),
  k) adding chlorosolvent to the solid,
  l) slowly adding the mixture obtained in step-(k) to hydrocarbon solvent,
  m) stirring the reaction mixture,
  n) filtering the solid and then drying to get amorphous form of compound of formula-1.

The fourteenth aspect of the present invention is to provide a novel crystalline benzylated posaconazole compound of formula-21, herein designated as form-M.

The fifteenth aspect of the present invention is to provide a novel crystalline form of triazole antifungal compound of formula-1, herein designated as form-S.

The sixteenth aspect of the present invention is to provide a process for the preparation of crystalline form-S of triazole antifungal compound of formula-1, comprising of:
  a) Debenzylating the benzylated posaconazole compound of formula-21 with Pd/C under hydrogen pressure in the presence of mineral acid in a suitable alcoholic solvent to provide the compound of formula-1,
  b) filtering the reaction mixture,
  c) adding a suitable organic solvent to the reaction mixture,
  d) cooling the reaction mixture to 10 to 15° C.,
  e) adjusting pH of the reaction mixture,
  f) isolating the solid by adding purified water to the reaction mixture,
  g) stirring the reaction mixture,
  h) filtered the solid and washing with purified water to get the crystalline form-S of compound of formula-1.

The seventeenth aspect of the present invention is to provide a novel crystalline form of triazole antifungal compound of formula-1, herein designated as form-N.

The eighteenth aspect of the present invention is to provide a process for the preparation of crystalline form-N of triazole antifungal compound of formula-1, comprising of:
  a) Dissolving the compound of formula-1 in acetone,
  b) heating the reaction mixture to reflux,
  c) filtering the reaction mixture,
  d) adding purified water to the filtrate,
  e) stirring the reaction mixture to obtain solid,
  f) filtered the solid and washing with purified water to get crystalline form-N of compound of formula-1.

BRIEF DESCRIPTION OF DRAWINGS

FIG. 5: Illustrates the PXRD pattern of crystalline form-N of posaconazole compound of formula-1 obtained as per the example-22.

DETAILED DESCRIPTION OF THE INVENTION

Figure 1:
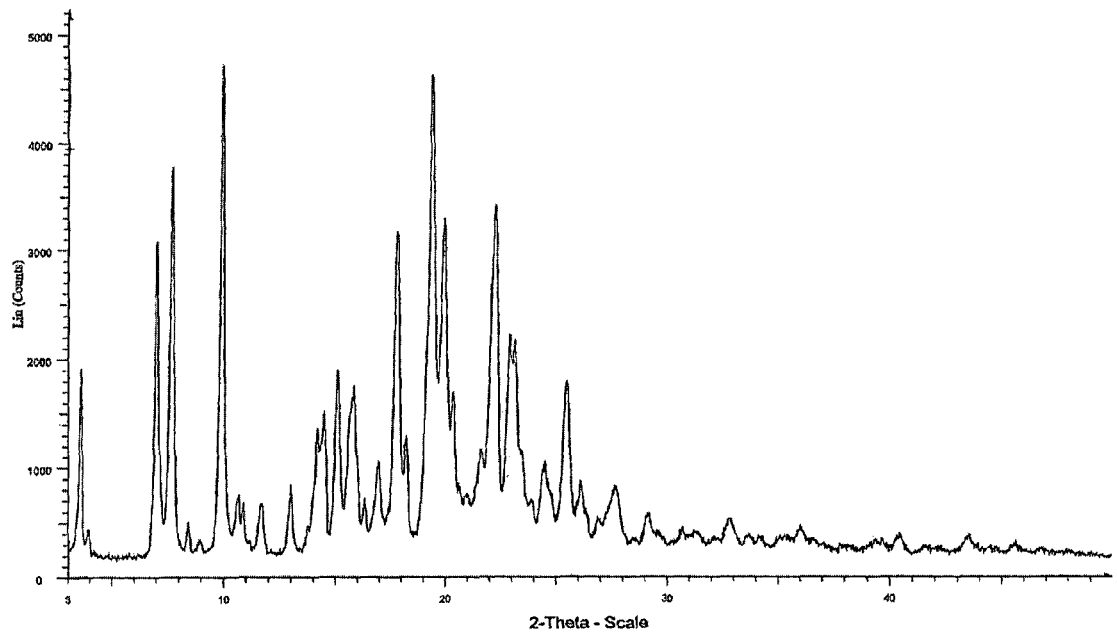
FIG. 1: Illustrates the PXRD pattern of isopropanol solvate crystalline form of posaconazole obtained as per the example-18.
Figure 2:
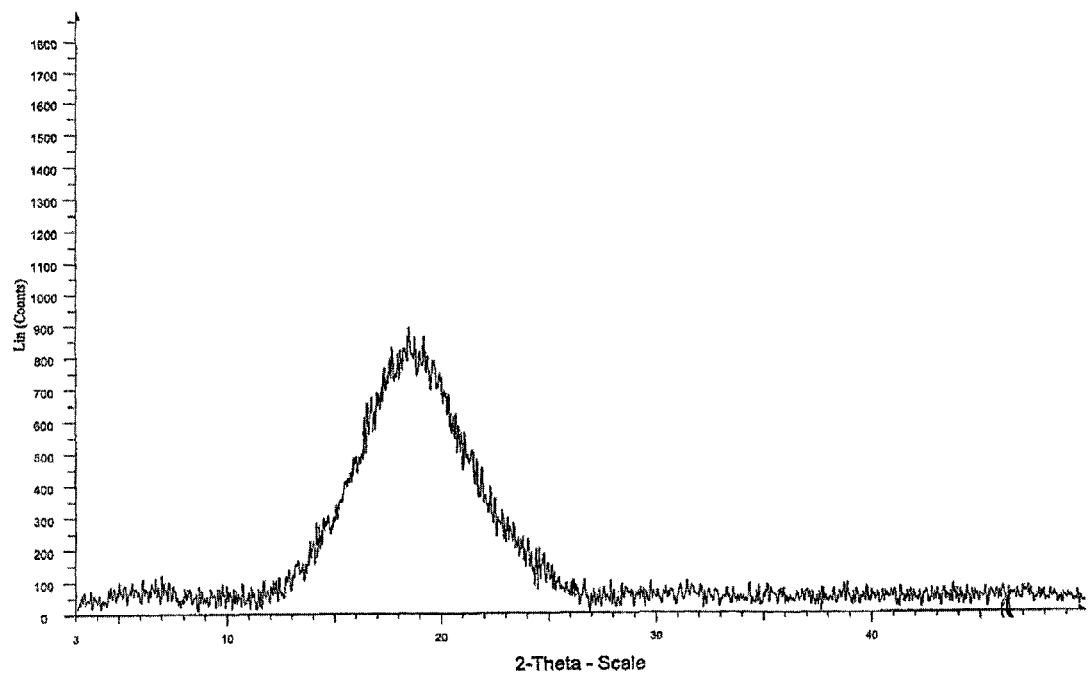
FIG. 2: Illustrates the PXRD pattern of amorphous form of compound of formula-21 obtained as per the example-19.

As used herein the term "alcoholic solvent" refers to methanol, ethanol, isopropyl alcohol, n-propanol, butanol and the like; "ester solvents" refers to ethyl acetate, methyl acetate, n-butyl acetate, isobutyl acetate, sec-butyl acetate, isopropyl acetate and the like, "ether solvents" like tetrahydrofuran, diethylether, methyltert-butylether, dioxane and the like; the term "hydrocarbon solvents" refers to toluene, xylene, cyclohexane, hexane, heptane, n-pentane and the like; the term "chloro solvents" refers to methylene chloride, ethylene dichloride, carbon tetra chloride, chloroform and the like; "polar aprotic solvents" refers to dimethylformamide, dimethylacetamide, dimethylsulfoxide and the like; the term "nitrile solvents" refers to acetonitrile and the like; "ketone solvents" refers to acetone, methyl isobutyl ketone and the like.

As used herein the present invention, the term "anti-solvent" refers to a solvent which is used to precipitate the solid from a solution and the suitable anti-solvent used herein the present invention is hydrocarbon solvent.

As used herein the term "base" is selected from inorganic bases like alkali metal hydroxides such as lithium hydroxide, sodium hydroxide, potassium hydroxide; alkali metal alkoxides such as sodium tert-butoxide, potassium tert-butoxide; alkali metal carbonates like sodium carbonate, potassium carbonate; alkali metal bicarbonates like sodium bicarbonate and potassium bicarbonate and organic bases like triethylamine, isopropyl ethylamine, diisopropyl amine, diisopropylethylamine, piperidine, pyridine, tributyl amine, 4-dimethylaminopyridine, N-methyl morpholine and the like.

As used herein the term "base" is selected from aqueous inorganic bases like alkali metal hydroxides, alkali metal alkoxides, alkali metal carbonates, alkali metal bicarbonates.

As used herein the term suitable "mineral acid" is selected from hydrochloric acid, hydrobromic acid, hydroiodic acid and sulfuric acid.

As used herein the term "activating agent" refers to thionyl chloride, oxalyl chloride, pivaloyl chloride, carbonylditriazole, oxalylditriazole, $POCl_3$, $PCl_3$, $PCl_5$ and $SOCl_2$.

As used herein the term "reducing agents" refers to DIBAL-H, lithiumaluminiumhydride, sodiumborohydride, lithiumborohydride, $NaBH_3CN$, sodiumborohydride/$BF_3$-etherate, vitride, sodium borohydride/aluminium chloride or borane/aluminium chloride, sodiumborohydride/iodine and 9-BBN.

As used herein, the term "alkyl" or "alkoxy" refers to straight chain or branched hydrocarbon groups, generally having specified number of carbon atoms. A "$C_{1-6}$ alkyl" refers to alkyl group having 1 to 6 carbon atoms. Examples of alkyl groups include, without limitation, methyl, ethyl, n-propyl, iso-propyl, n-butyl, sec-butyl, iso-butyl, t-butyl and the like. A "$C_{1-6}$ alkoxy" refers to alkyl group having 1 to 6 carbon atoms attached to oxygen. Examples of alkoxy groups include, without limitation, methoxy, ethoxy, n-propyloxy, iso-propyloxy, n-butyloxy, sec-butyloxy, iso-butyloxy, t-butyloxy and the like.

The first aspect of the present invention is to provide a novel process for the preparation of (3S,5R)-5-(2,4-difluorophenyl)-5-(iodomethyl)tetrahydrofuran-3-carboxylic acid compound of formula-7, comprising of the following steps:

a) Reacting 4-(2,4-difluorophenyl)pent-4-enoic acid compound of formula-2

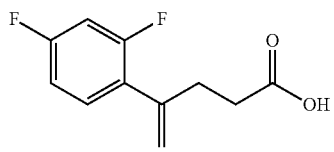

Formula-2 with (R)-4-phenyloxazolidin-2-one compound of formula-3

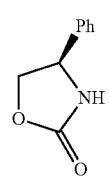

Formula-3 in the presence of a suitable activating agent and suitable base in a suitable solvent to provide (R)-3-(4-(2,4-difluorophenyl)pent-4-enoyl)-4-phenyl oxazolidin-2-one compound of formula-4,

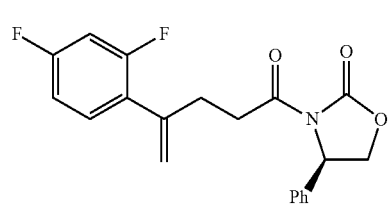

Formula-4 b) hydroxy methylating the compound of formula-4 with 1,3,5-trioxane in the presence of a base and a suitable catalyst in a suitable solvent to provide (R)-3-((S)-4-(2,4-difluorophenyl)-2-(hydroxymethyl)pent-4-enoyl)-4-phenyloxazolidin-2-one compound of formula-5,

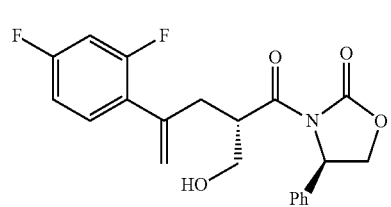

Formula-5 c) cyclizing the compound of formula-5 in-situ in the presence of iodine and a suitable base in a suitable solvent to provide (R)-3-((3S,5R)-5-(2,4-difluoro phenyl)-5-(iodomethyl)tetrahydrofuran-3-carbonyl)-4-phenyloxazolidin-2-one compound of formula-6,

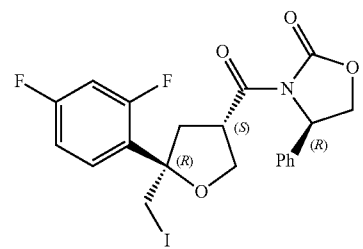

Formula-6 d) hydrolyzing the compound of formula-6 with a suitable base in the presence of a suitable catalyst in a suitable solvent to provide (3S,5R)-5-(2,4-difluorophenyl)-5-(iodomethyl)tetrahydrofuran-3-carboxylic acid compound of formula-7.

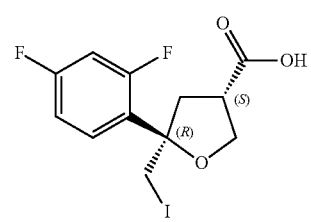

Formula-7

Wherein;
in step-a) suitable activating agent is selected from thionyl chloride, oxalyl chloride, pivaloyl chloride, carbonylditriazole, oxalylditriazole, $POCl_3$, $PCl_3$, $PCl_5$ and $SO_2Cl_2$; the suitable base is selected from organic base such as triethylamine, tributyl amine, pyridine, 4-dimethylaminopyridine, N-methyl morpholine and diisopropylethyl amine; and the suitable solvent is selected from chloro solvents, polar aprotic solvents, alcoholic solvents and mixture thereof.

in step-b) the suitable base is selected from organic bases such as triethylamine, tributyl amine, pyridine, 4-dimethylaminopyridine, N-methyl morpholine and diisopropylethyl amine; and the suitable solvent is selected from chloro solvents, ketone solvents, ester solvents and mixture thereof and the suitable catalyst is TiCl4.

in step-c) the suitable base is selected from inorganic bases such as alkali metal hydroxides, alkali metal alkoxides, alkali metal carbonates and alkali metal bicarbonates; and the suitable solvent is selected from chloro solvents, ether solvents, alcoholic solvents and mixture thereof.

in step-d) the suitable catalyst is preferably hydrogen peroxide and the suitable base is selected from inorganic bases such as alkali metal hydroxides, alkali metal alkoxides, alkali metal carbonates, alkali metal bicarbonates and the suitable solvent is selected from ether solvents, ketone solvents and hydrocarbon solvents.

In a preferred embodiment of the present invention is to provide a novel process for the preparation of (3S,5R)-5-(2,4-difluorophenyl)-5-(iodomethyl)tetrahydrofuran-3-carboxylic acid compound of formula-7, comprising of the following steps:
a) Reacting the 4-(2,4-difluorophenyl)pent-4-enoic acid compound of formula-2 with (R)-4-phenyloxazolidin-2-one compound of formula-3 in the presence of pivaloyl chloride, 4-dimethylaminopyridine and triethylamine in a mixture of dimethylformamide and dichloromethane to provide (R)-3-(4-(2,4-difluoro phenyl)pent-4-enoyl)-4-phenyloxazolidin-2-one compound of formula-4,
b) hydroxy methylating the compound of formula-4 using 1,3,5-trioxane in the presence of titanium tetrachloride and diisopropylethylamine in dichloromethane provides (R)-3-((S)-4-(2,4-difluorophenyl)-2-(hydroxymethyl)pent-4-enoyl)-4-phenyloxazolidin-2-one compound of formula-5,
c) cyclizing the compound of formula-5 in-situ in the presence of iodine and sodium carbonate in a mixture of tetrahydrofuran, methyl tertiarybutyl ether and isopropanol to provide (R)-3-((3S,5R)-5-(2,4-difluorophenyl)-5-(iodomethyl) tetrahydrofuran-3-carbonyl)-4-phenyloxazolidin-2-one compound of formula-6,
d) hydrolyzing the compound of formula-6 with NaOH in the presence of hydrogen peroxide in tetrahydrofuran and cyclohexane to provide (3S,5R)-5-(2,4-difluoro phenyl)-5-(iodomethyl)tetrahydrofuran-3-carboxylic acid compound of formula-7.

The mole ratio of hydrogen peroxide used in step-d) of the above aspect is in between 1.0→2.0, preferably between 1.0→1.5, most preferably between 1.0→1.25 with respect to the compound of formula-6.

U.S. Pat. No. 5,403,937 disclosed the usage of base like pyridine in step-a) and step-c) of the above aspect. As pyridine is carcinogenic in nature hence is not advisable for the commercial scale-up process. Whereas, the present process uses bases like 4-dimethylamino pyridine in step a) and sodium carbonate in step-c) respectively which are safer and easy to handle in the laboratory as well as in the commercial scale-up process. Hence the present process is advantageous over the prior art process.

The second aspect of the present invention is to provide a novel process for the preparation of (R)-3-((S)-4-(2,4-difluorophenyl)-2-(hydroxymethyl)pent-4-enoyl)-4-phenyloxazolidin-2-one compound of formula-5, comprising of:
a) Reacting 4-(2,4-difluorophenyl)pent-4-enoic acid compound of formula-2 with (R)-4-phenyloxazolidin-2-one compound of formula-3 in the presence of a suitable activating agent and suitable base in a suitable solvent to provide (R)-3-(4-(2,4-difluorophenyl)pent-4-enoyl)-4-phenyloxazolidin-2-one compound of formula-4,
b) hydroxy methylating the compound of formula-4 with 1,3,5-trioxane in the presence of a base and a suitable catalyst in a suitable solvent to provide (R)-3-((S)-4-(2,4-difluorophenyl)-2-(hydroxymethyl)pent-4-enoyl)-4-phenyloxazolidin-2-one compound of formula-5 as residue, which is optionally isolated as solid from a suitable solvent.
wherein, the suitable solvent used for the isolation of compound of formula-5 in step-(b) is alcohol solvent, preferably isopropyl alcohol.

In a preferred embodiment of the present invention is to provide a novel process for the preparation of (R)-3-((S)-4-(2,4-difluorophenyl)-2-(hydroxymethyl)pent-4-enoyl)-4-phenyloxazolidin-2-one compound of formula-5, comprising of:
a) Reacting the 4-(2,4-difluorophenyl)pent-4-enoic acid compound of formula-2 with (R)-4-phenyloxazolidin-2-one compound of formula-3 in the presence of pivaloyl chloride, 4-dimethylaminopyridine and triethylamine in dimethyl formamide and dichloromethane to provide (R)-3-(4-(2,4-difluoro phenyl)pent-4-enoyl)-4-phenyloxazolidin-2-one compound of formula-4,
b) hydroxy methylating the compound of formula-4 using 1,3,5-trioxane in the presence of titanium tetrachloride and diisopropylethylamine in dichloromethane provides (R)-3-((S)-4-(2,4-difluorophenyl)-2-(hydroxymethyl) pent-4-enoyl)-4-phenyloxazolidin-2-one compound of formula-5 as residue, which is isolated as a solid from isopropyl alcohol.

The third aspect of the present invention is to provide a process for the preparation of ((3R,5R)-5-(2,4-difluorophenyl)-5-(iodomethyl)tetrahydrofuran-3-yl) methanol compound of formula-8, comprising of:
a) Hydrolyzing the (R)-3-((3S,5R)-5-(2,4-difluorophenyl)-5-(iodomethyl)tetrahydro furan-3-carbonyl)-4-phenyloxazolidin-2-one compound of formula-6 with a suitable base in the presence of a catalyst in a suitable solvent to provide (3S,5R)-5-(2,4-difluorophenyl)-5-(iodomethyl)tetrahydrofuran-3-carboxylic acid compound of formula-7,
b) reducing the compound of formula-7 with a suitable reducing agent in a suitable solvent to provide ((3R,5R)-5-(2,4-difluorophenyl)-5-(iodomethyl)tetrahydro furan-3-yl)methanol compound of formula-8.

wherein;
in step-a) the suitable catalyst is preferably hydrogen peroxide and the suitable base is selected from inorganic bases such as alkali metal hydroxides, alkali metal alkoxides, alkali metal carbonates, alkali metal bicarbonates and the suitable solvent is selected from ether solvents, ketone solvents, hydrocarbon solvents and polar solvents or mixtures thereof.
in step-b) the suitable reducing agent is selected from DIBAL-H, lithium aluminiumhydride, sodiumborohydride, lithiumborohydride, $NaBH_3CN$, sodiumborohydride/$BF_3$-etherate, vitride, sodium borohydride/aluminium chloride or borane/aluminiumchloride, sodiumborohydride/iodine and 9-BBN and the suitable solvent is selected from ether solvent, ester solvents, hydrocarbon solvents and ketone solvents.

In a preferred embodiment of the present invention is to provide an improved process for the preparation of ((3R,5R)-5-(2,4-difluorophenyl)-5-(iodomethyl)tetrahydro furan-3-yl)methanol compound of formula-8, which comprising of the following steps:

a) Hydrolyzing the compound of formula-6 with sodium hydroxide in the presence of hydrogen peroxide in tetrahydrofuran to provide (3S,5R)-5-(2,4-difluoro phenyl)-5-(iodomethyl)tetrahydrofuran-3-carboxylic acid compound of formula-7, b) reducing the compound of formula-7 with sodiumborohydride in the presence of $BF_3$-etherate in tetrahydrofuran to provide ((3R,5R)-5-(2,4-difluorophenyl)-5-(iodomethyl)tetrahydrofuran-3-yl)methanol compound of formula-8.

U.S. Pat. No. 5,403,937 describes the reduction of compound of formula-6 using lithium chloride/sodiumborohydride to provide the compound of formula-8 with lower purity. The obtained compound contains impurities and 4-benzyloxazolidin-2one as a bi-product, which requires tedious purification process to get the pure compound.

In the process of the present invention, compound of formula-6 is hydrolyzed in the presence of suitable base and a catalyst to provide (3S,5R)-5-(2,4-difluorophenyl)-5-(iodomethyl)tetrahydrofuran-3-carboxylic acid compound of formula-7 with enhanced percentage of yield and purity. Further the compound of formula-7 is reduced in the presence of sodiumborohydride/BF3-etherate to provide compound of formula-8 without the formation of 4-phenyloxazolidin-2-one as a bi-product, which results in the increase in the yield and purity of compound of formula-8. Hence the process of the present invention is more advantageous over the prior art process.

The fourth aspect of the present invention is to provide a novel process for the preparation of ((3S,5R)-5-((1H-1,2,4-triazol-1-yl)methyl)-5-(2,4-difluorophenyl)tetra hydrofuran-3-yl)methyl 4-methylbenzenesulfonate compound of formula-10, which comprising the following steps:

a) Reacting the 4-(2,4-difluorophenyl)pent-4-enoic acid compound of formula-2 with (R)-4-phenyloxazolidin-2-one compound of formula-3 in the presence of suitable activating agent and a suitable base in a suitable solvent to provide (R)-3-(4-(2,4-difluorophenyl)pent-4-enoyl)-4-phenyloxazolidin-2-one compound of formula-4, b) hydroxy methylating the compound of formula-4 with 1,3,5-trioxane in the presence a base and a suitable catalyst in a suitable solvent to provide (R)-3-((S)-4-(2,4-difluorophenyl)-2-(hydroxymethyl)pent-4-enoyl)-4-phenyloxazolidin-2-one compound of formula-5, c) cyclizing the compound of formula-5 in-situ in the presence of iodine and a suitable base in a suitable solvent to provide (R)-3-((3S,5R)-5-(2,4-difluorophenyl)-5-(iodomethyl)tetrahydrofuran-3-carbonyl)-4-phenyloxazolidin-2-one compound of formula-6, d) hydrolyzing the compound of formula-6 with a suitable base in the presence of a suitable catalyst in a suitable solvent to provide (3S,5R)-5-(2,4-difluorophenyl)-5-(iodomethyl)tetrahydrofuran-3-carboxylic acid compound of formula-7, e) reducing the compound of formula-7 with a suitable reducing agent in a suitable solvent to provide ((3R,5R)-5-(2,4-difluorophenyl)-5-(iodomethyl)tetrahydro furan-3-yl)methanol compound of formula-8, f) reacting the compound of formula-8 with 1H-1,2,4-triazole (free base) in the presence of a suitable base in a suitable solvent to provide ((3R,5R)-5-((1H-1,2,4-triazol-1-yl)methyl)-5-(2,4-difluorophenyl)tetrahydrofuran-3-yl)methanol compound of formula-9, g) reacting the compound of formula-9 in-situ with p-toluenesulfonyl chloride in the presence of a suitable base in a suitable solvent to provide ((3S,5R)-5-((1H-1,2,4-triazol-1-yl)methyl)-5-(2,4-difluorophenyl)tetrahydrofuran-3-yl)methyl 4-methyl benzene sulfonate compound of formula-10.

Wherein;

The reagents, catalysts, solvents and bases used in step-(a) to step-(d) of the present aspect is same as defined in first aspect of the present invention;

in step-e) the suitable reducing agent is selected from DIBAL-H, lithium aluminium hydride, sodiumborohydride, lithiumborohydride, $NaBH_3CN$, sodium boro hydride/$BF_3$-etherate, vitride, sodium borohydride/aluminium chloride or borane/aluminiumchloride, sodiumborohydride/iodine and 9-BBN; and the suitable solvent is selected from ether solvent, ester solvents, hydrocarbon solvents and ketone solvents.

in step-f) the suitable base is selected from inorganic base or organic base as defined above and the suitable solvent is selected from polar aprotic solvents, chloro solvents, alcoholic solvents and hydrocarbon solvents or mixture thereof.

in step-g) the suitable base is selected from organic base as defined above and the suitable solvent is selected from chloro solvents, alcoholic solvents and hydrocarbon solvents In a preferred embodiment of the present invention is to provide a novel process for the preparation of ((3S,5R)-5-((1H-1,2,4-triazol-1-yl)methyl)-5-(2,4-difluorophenyl) tetrahydrofuran-3-yl)methyl 4-methylbenzene sulfonate compound of formula-10, comprising of the following steps:

a) Reacting the 4-(2,4-difluorophenyl)pent-4-enoic acid compound of formula-2 with (R)-4-phenyloxazolidin-2-one compound of formula-3 in the presence of pivaloyl chloride, DMAP and TEA (triethylamine) in a mixture of dimethylformamide and dichloromethane to provide (R)-3-(4-(2,4-difluorophenyl)pent-4-enoyl)-4-phenyloxazolidin-2-one compound of formula-4, b) hydroxy methylating the compound of formula-4 using 1,3,5-trioxane in the presence of titanium tetrachloride and diisopropylethylamine in dichloromethane provides (R)-3-((S)-4-(2,4-difluorophenyl)-2-(hydroxymethyl)pent-4-enoyl)-4-phenyloxazolidin-2-one compound of formula-5, c) cyclizing the compound of formula-5 in-situ in the presence of iodine and sodium carbonate in dichloromethane to provide (R)-3-((3S,5R)-5-(2,4-difluorophenyl)-5-(iodomethyl)tetrahydrofuran-3-carbonyl)-4-phenyloxazolidin-2-one compound of formula-6, d) hydrolyzing the compound of formula-6 with NaOH in the presence of hydrogen peroxide in tetrahydrofuran and cyclohexane to provide (3S,5R)-5-(2,4-difluorophenyl)-5-(iodomethyl)tetrahydrofuran-3-carboxylic acid compound of formula-7, e) reducing the compound of formula-7 with sodiumborohydride in the presence of $BF_3$-etherate in tetrahydrofuran to provide ((3R,5R)-5-(2,4-difluorophenyl)-5-(iodomethyl)tetrahydrofuran-3-yl)methanol compound of formula-8, f) reacting the compound of formula-8 with 1H-1,2,4-triazole (freebase) in the presence of sodium tertiarybutoxide and dimethylaminopyridine in dimethylformamide and dichloromethane to provide ((3R,5R)-5-((1H-1,2,4-triazol-1-yl)methyl)-5-(2,4-difluorophenyl)tetrahydrofuran-3-yl)methanol compound of formula-9, g) reacting the compound of formula-9 in-situ with p-toluenesulfonyl chloride in-situ in the presence of 4-dimethylamino pyridine in dichloromethane to provide ((3S,5R)-5-((1H-1,2,4-triazol-1-yl)methyl)-5-(2,4-difluorophenyl)tetrahydrofuran-3-yl)methyl-4-methyl benzenesulfonate compound of formula-10.

U.S. Pat. No. 5,403,937 disclosed the process for the preparation of compound of formula-9, which involves reacting the compound of formula-8 with sodium triazole and DMPU to provide compound of formula-9. As sodium triazole is unstable and is prepared at the time of the reaction. And the usage of DMPU reagent in the reaction takes longer time for the completion of the reaction and thereby the compound of formula-9 is formed with low yield with DMPU as impurity, hence it requires tedious purification process to get the pure compound of formula-9.

The present invention is carried out by reacting the compound of formula-8 with triazole (free base), in the presence of base like 4-dimethylaminopyridine, due to which the reaction completes in short period of time and the product formed with enhanced yield as well as purity. Hence the present process has improvement over the prior art process.

U.S. Pat. No. 5,403,937 also disclosed the usage of base like pyridine in step-g) which is not advisable to be use in the laboratory process and especially at commercial scale-up process, as it is carcinogenic in nature.

The process of the present invention involves the usage of base like 4-dimethylaminopyridine, which is safer and easy to use in the laboratory as well as in the commercial scale-up process.

The fifth aspect of the present invention is to provide novel intermediate compounds which are useful in the preparation of anti-fungal drug of compound of formula-1. The said novel intermediates include:
a) (R)-3-(4-(2,4-difluorophenyl)pent-4-enoyl)-4-phenyloxazolidin-2-one compound of formula-4;
b) (R)-3-((S)-4-(2,4-difluorophenyl)-2-(hydroxymethyl) pent-4-enoyl)-4-phenyl oxazolidin-2-one compound of formula-5;
c) (R)-3-((3S,5R)-5-(2,4-difluorophenyl)-5-(iodomethyl) tetrahydrofuran-3-carbonyl)-4-phenyl oxazolidin-2-one compound of formula-6;
d) (3S,5R)-5-(2,4-difluorophenyl)-5-(iodomethyl)tetrahydrofuran-3-carboxylic acid compound of formula-7.

The sixth aspect of the present invention is to provide an improved process for the preparation of (S)—N'-(2-(benzyloxy)propylidene)formylhydrazide compound of formula-16,

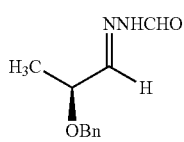

Formula-16 comprising of the following steps:
a) Reacting the racemic methyl lactate compound of formula-11

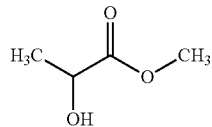

Formula-11 with benzyl chloride in the presence of a suitable base in a suitable solvent to provide methyl 2-(benzyloxy) propanoate compound of formula-12,

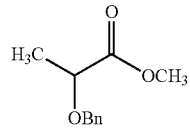

Formula-12 b) hydrolyzing the compound of formula-12 in-situ with aqueous base in a suitable solvent to provide 2-(benzyloxy)propanoic acid compound of formula-13,

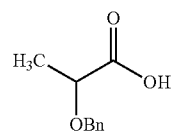

Formula-13 c) resolving the compound of formula-13 in-situ with (S)-1-phenylethanamine in a suitable solvent to provide (S)-1-phenylethanamine salt of (S)-2-(benzyloxy) propanoic acid compound of formula-13a,

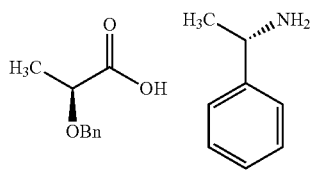

Formula-13a d) reacting the compound of formula-13a with a alcoholic solvent in presence of a suitable activating agent in a suitable solvent to provide (S)-methyl 2-(benzyloxy) propanoate compound of formula-14,

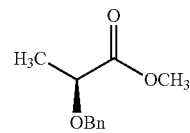

Formula-14 e) reducing the compound of formula-14 with a suitable reducing agent in a suitable solvent to provide (S)-2-(benzyloxy)propanal compound of formula-15,

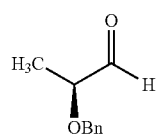

Formula-15 f) reacting the compound of formula-15 in-situ with formyl hydrazine in a suitable solvent to provide (S)—N'-(2-(benzyloxy)propylidene)formohydrazide compound of formula-16.

Wherein;
in step-a) the suitable base is inorganic base and suitable polar aprotic solvent is selected from dimethylformamide, dimethylacetamide and dimethylsulfoxide.
in step-b) the base is selected from aqueous inorganic base and the suitable solvent is selected from hydrocarbon solvents or chloro solvents.
in step-c) the suitable solvent is selected from hydrocarbon solvents.
in step-d) the suitable activating agent is thionyl chloride and the suitable solvent is selected from alcoholic solvents and polar aprotic solvents.
in step-e) the suitable reducing agent is DIBAL-H and the suitable solvent is hydrocarbon solvent.
in step-f) the suitable solvent is selected from alcoholic solvents.

In a preferred embodiment of the present invention is to provide an improved process for the preparation of (S)—N'-(2-(benzyloxy)propylidene)formylhydrazide compound of formula-16, comprising of:
a) Reacting the racemic methyl lactate compound of formula-11 with benzyl chloride in the presence of sodiumtertiarybutoxide in dimethylformamide to provide methyl 2-(benzyloxy)propanoate compound of formula-12,
b) hydrolyzing the compound of formula-12 in-situ with aqueous sodium hydroxide in toluene to provide 2-(benzyloxy)propanoic acid compound of formula-13,
c) resolving the compound of formula-13 in-situ with (S)-phenyl ethylamine in toluene to provide (S)-1-phenylethanamine salt of (S)-2-(benzyloxy)propanoic acid compound of formula-13a,
d) reacting the compound of formula-13a with methanol in presence of thionyl chloride in dimethylformamide to provide (S)-methyl 2-(benzyloxy)propanoate compound of formula-14,
e) reducing the compound of formula-14 with DIBAL-H in toluene to provide (S)-2-(benzyloxy)propanal compound of formula-15,
f) reacting the compound of formula-15 in-situ with formyl hydrazine in methanol to provide (S)—N'-(2-(benzyloxy)propylidene)formohydrazide compound of formula-16.

In the above aspect the racemic 2-(benzyloxy)propanoic acid compound of formula-13 can be resolved using the compound of general formula-22

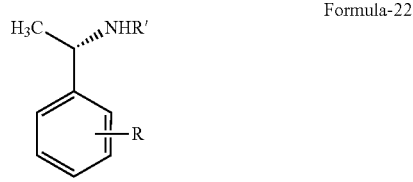

Formula-22 to provide the compound of formula-23.

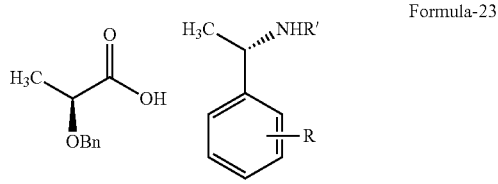

Formula-23 wherein, R is selected from CN, hydroxy, F, Cl, Br, I, $C_1$-$C_6$ alkyl, $C_1$-$C_6$ alkoxy; R' is selected from H, $C_1$-$C_6$ alkyl;

The seventh aspect of the present invention is to provide (S)-1-phenylethanamine salt of (S)-2-(benzyloxy) propanoic acid compound of formula-13a, a novel intermediate compound which is useful in the preparation of (S)—N'-(2-(benzyloxy)propylidene) formylhydrazide compound of formula-16.

The eighth aspect of the present invention is to provide an improved process for the preparation of phenyl 4-(4-(4-hydroxyphenyl)piperazin-1-yl)phenylcarbamate compound of formula-19, which comprises of reacting 4-(4-(4-aminophenyl)piperazin-1-yl)phenol compound of formula-18 with arylchloroformate in a suitable solvent to provide phenyl 4-(4-(4-hydroxyphenyl)piperazin-1-yl)phenylcarbamate compound of formula-19.

Wherein, the suitable arylchloroformate is phenylchloroformate and suitable solvent is polar aprotic solvent selected from dimethylformamide, dimethylacetamide and dimethylsulfoxide, preferably dimethylformamide.

U.S. Pat. No. 5,625,064 describes the process for the preparation of phenyl 4-(4-(4-hydroxyphenyl)piperazin-1-yl)phenylcarbamate compound of formula-19 in the presence of a base like pyridine, which is not advisable to use in the laboratory and especially at commercial scale-up process, as it is carcinogenic in nature. Whereas, the present invention describes the preparation of compound of formula-19 in the absence of base. Hence the present invention has improvement over the prior art.

The ninth aspect of the present invention is to provide an improved process for the preparation of pure Triazole derivative compound of formula-1, comprising of the following steps:
a) Reacting the (S)—N'-(2-(benzyloxy)propylidene)formohydrazide compound of formula-16 with ethyl magnesium halide in the presence of bis(trimethylsilyl)acetamide in a suitable solvent to provide N'-((2S,3S)-2-(benzyloxy)pentan-3-yl)formohydrazide compound of formula-17,
b) reacting the compound of formula-17 in-situ with phenyl 4-(4-(4-hydroxyphenyl)piperazin-1-yl)phenylcarbamate compound of formula-19 in the presence of suitable base in a suitable solvent to provide 1-((2S,3S)-2-(benzyloxy)pentan-3-yl)-4-(4-(4-(4-hydroxyphenyl)piperazin-1-yl)phenyl)-1H-1,2,4-triazol-5(4H)-one compound of formula-20,
c) condensing the compound of formula-20 with ((3S,5R)-5-((1H-1,2,4-triazol-1-yl)methyl)-5-(2,4-difluorophenyl)tetrahydrofuran-3-yl)methyl-4-methyl benzenesulfonate compound of formula-10,

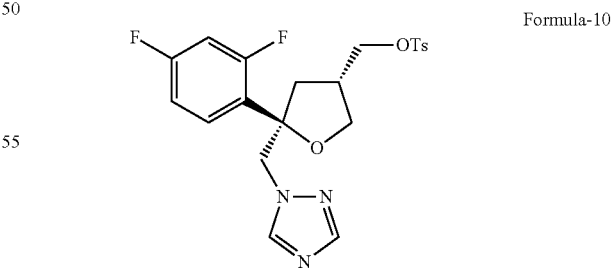

Formula-10 in the presence of base in a suitable polar aprotic solvent to provide 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy) pentan-3-yl)-1H-1,2,4-triazol-5(4H)-one compound of formula-21, d) debenzylating the compound of formula-21 with Pd/C under hydrogen pressure in the presence of mineral acid in a suitable alcoholic solvent to provide Triazole derivative compound of formula-1, e) optionally, purifying the compound obtained in step-(d) from a suitable solvent to provide pure compound of formula-1.

Wherein, in step-a) the suitable solvent is ether solvent is selected from methyl tertiary butyl ether, tetrahydrofuran, diethyl ether, methyl tert-butyl ether, dioxane, preferably methyl tert-butyl ether.

in step-b) the suitable base is selected from organic base and the suitable solvent is selected from ether solvents, hydrocarbon solvents and ketone solvents, preferably dioxane.

in step-c) the suitable base is selected from inorganic base and the suitable solvent is selected from polar aprotic solvents, ester solvents or mixture thereof.

in step-d) the suitable mineral acid is selected from hydroiodic acid, sulfuric acid and hydrochloric acid and a suitable alcoholic solvent is selected from methanol, ethanol, isopropanol and butanol.

in step-e) the suitable solvent is selected from alcoholic solvent.

The present process involves in-situ reaction of the formylhydrazine derivative of formula-17 with phenylcarbamate compound of formula-19, which provides compound of formula-20 with enhanced purity as well as yield. Hence the present invention is more advantageous over the prior art processes.

Further, the purification of compound of fomula-20 using methanol enhanced the purity from 97.67% to 99.15% and also reduces the content of desbenzyloxy phenol (herein designated as "impurity-A") from 0.37% to 0.09%. In the prior art processes the desbenzyloxy phenol impurity was formed due to chemical degradation and further the formed impurity was reacted with compound of formula-10 provides the deshydroxy posaconazole as an impurity in the final product. Whereas, in the present invention the desbenzyloxy phenol impurity is arrested at the origin itself thereby produces the pure posaconazole with 99.85% purity and controls the deshydroxy posaconazole impurity-B in the final product to the acceptable levels.

The desbenzyloxy phenol and deshydroxy posaconazole impurities are represented by the following structural formulas:

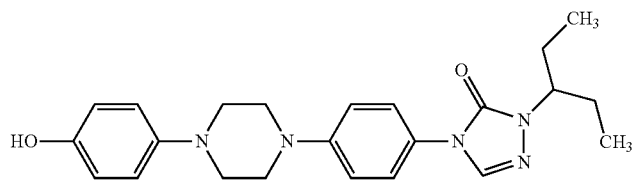

Desbenzyloxy phenol ("Impurity-A")

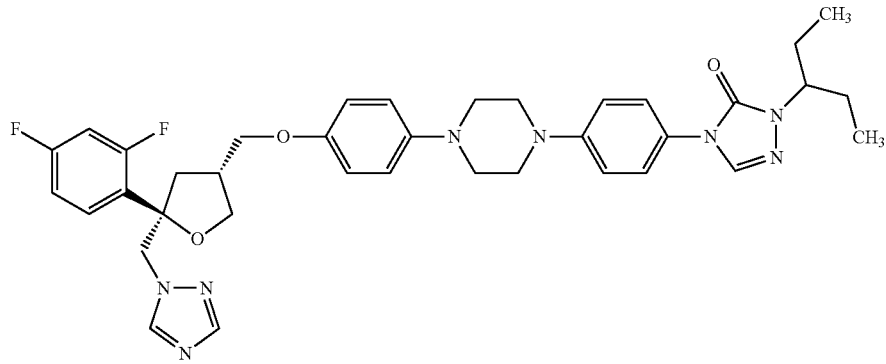

Deshydroxy posaconazole ("Impurity-B")

U.S. Pat. No. 5,625,064 disclosed a process for the deprotection of benzyl ether of posaconazole in the presence of formic acid requires 30-35 hours of time period for completion of the reaction. This may lead to degradation of final product and may require tedious purification processes such as chromatography purification. Whereas, the present invention avoids the usage of formic acid for the deprotection of compound of formula-21 and uses Pd/C and methanol for deprotection. The present invention also involves the condensation of compound of formula-20 with highly pure compound of formula-10 resulting the compound of formula-21 with high purity and yield, which inturn enhances the posaconazole compound of fomula-1 with 99.8% purity. Henceforth, the process of the present invention is more advantageous over the prior known processes.

The tenth aspect of the present invention is to provide an improved process for the preparation of 4-(4-(4-(4-(((3R, 5R)-5-((1H-1,2,4-triazol-1-yl)methyl)-5-(2,4-difluoro phenyl)tetrahydrofuran-3-yl)methoxy)phenyl)piperazin-1-yl) phenyl)-1-((2S,3S)-2-(benzyloxy)pentan-3-yl)-1H-1,2,4-triazol-5(4H)-one compound of formula-21, which comprises of condensing 1-((2S,3S)-2-(benzyloxy)pentan-3-yl)-4-(4-(4-(4-hydroxy phenyl)piperazin-1-yl)phenyl)-1H-1, 2,4-triazol-5(4H)-one compound of formula-20 with ((3S, 5R)-5-((1H-1,2,4-triazol-1-yl)methyl)-5-(2,4- difluorophenyl)tetrahydrofuran-3-yl)methyl-4-methyl benzenesulfonate compound of formula-10 in the presence of a suitable base preferably sodium hydroxide in a suitable solvent preferably dimethyl sulfoxide to provide compound of formula-21.

The prior reported processes for the preparation of compound of formula-21, involves the usage of sodium hydride (NaH) in the coupling reaction, which is pyrophoric in nature, difficult to handle and not suitable for commercial purposes. Whereas, the process of the present invention involves the usage of sodium hydroxide base and dimethyl sulfoxide solvent, which are simple, easily available and suitable for commercial scale process.

The eleventh aspect of the present invention is to provide an improved process for the preparation of amorphous 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one compound of formula-21, comprising of:
  a) Condensing the 1-((2S,3S)-2-(benzyloxy)pentan-3-yl)-4-(4-(4-(4-hydroxy phenyl)piperazin-1-yl)phenyl)-1H-1,2,4-triazol-5(4H)-one compound of formula-20 with ((3S,5R)-5-((1H-1,2,4-triazol-1-yl)methyl)-5-(2,4-difluorophenyl)tetra hydrofuran-3-yl)methyl-4-methyl benzenesulfonate compound of formula-10 in the presence of sodium hydroxide in dimethyl sulfoxide at 45-60° C. to provide the compound of formula-21,
  b) quenching the reaction mixture with water,
  c) neutralizing the reaction mixture with a suitable acid selected from organic acids such as benzene sulfonic acid, maleic acid, oxalic acid, fumaric acid, succinic acid, p-toluene sulfonic acid, malic acid and the like; or inorganic acids such as hydrochloric acid, hydrobromic acid, sulfuric acid, nitric acid and the like to provide amorphous compound of formula-21.

The twelfth aspect of the present invention is to provide a novel process for the preparation of amorphous 4-[4-[4-[4-[[(3R,5R)-5-(2,4-difluoro phenyl)tetrahydro-5-(1H-1,2,4-triazol-1-ylmethyl)-3furanyl]methoxy]phenyl]-1-piperazinyl]phenyl]-2-[(1S,2S)-1-ethyl-2-hydroxypropyl]-2,4-dihydro-3H-1,2,4-triazol-3-one compound of formula-1, which comprising of:
  a) Dissolving the compound of formula-1 in a suitable solvent,
  b) filtering the reaction mixture,
  c) adding the filtrate to a suitable anti-solvent such as non-polar solvent,
  d) stirring the reaction mixture,
  e) filtering the solid and then drying to get amorphous form of compound of formula-1.

Wherein, the suitable solvent used is selected from chloro solvents, ketone solvents, ester solvents, ether solvents, alcoholic solvents and the suitable anti-solvent is selected from non-polar solvents such as hydrocarbon solvents.

In a preferred embodiment of the present invention to provide a novel process for the preparation of amorphous 4-[4-[4-[4-[[(3R,5R)-5-(2,4-difluoro phenyl)tetrahydro-5-(1H-1,2,4-triazol-1-ylmethyl)-3furanyl]methoxy]phenyl]-1-piperazinyl]phenyl]-2-[(1S,2S)-1-ethyl-2-hydroxypropyl]-2,4-dihydro-3H-1,2,4-triazol-3-one compound of formula-1, which comprising of:
  a) Dissolving the compound of formula-1 in dichloromethane,
  b) filtering the reaction mixture,
  c) adding the filtrate to the n-pentane,
  d) stirring the reaction mixture,
  e) filtering the solid and then drying to get amorphous form of compound of formula-1.

The thirteenth aspect of the present invention is to provide a one-pot process for the preparation of amorphous 4-[4-[4-[4-[[(3R,5R)-5-(2,4-difluoro phenyl)tetrahydro-5-(1H-1,2,4-triazol-1-ylmethyl)-3 furanyl]methoxy]phenyl]-1-piperazinyl]phenyl]-2-[(1S,2S)-1-ethyl-2-hydroxypropyl]-2,4-dihydro-3H-1,2,4-triazol-3-one compound of formula-1, which comprising of:
  a) Reacting the 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one with Pd/C under hydrogen pressure in presence of mineral acid in a suitable solvent,
  b) filtering the reaction mixture and adding organic solvent to the filtrate,
  c) cooling the reaction mixture and adjusting the pH of the reaction mixture,
  d) adding water to the reaction mixture,
  e) filtering the precipitated solid,
  f) adding organic solvent to the solid, obtained in step-(e) and heating the reaction mixture,
  g) filtering the reaction mixture,
  h) adding water to the filtrate and stirring the reaction mixture,
  i) filtering the precipitated solid,
  j) optionally, purifying the obtained solid in step-(i),
  k) adding chlorosolvent to the solid,
  l) slowly adding the mixture obtained in step-(k) to hydrocarbon solvent,
  m) stirring the reaction mixture,
  n) filtering the solid and then drying to get amorphous form of compound of formula-1.

Wherein, the suitable solvent used in step-(b) & (f) is selected from ketone solvents, preferably acetone; the suitable solvent used in step-(k) is selected from chloro solvents, preferably dichloromethane; and the suitable solvent used in step-(l) is selected from non-polar solvents such as hydrocarbon solvents, preferably n-pentane.

In a preferred embodiment of the present invention to provide a one-pot process for the preparation of amorphous 4-[4-[4-[4-[[(3R,5R)-5-(2,4-difluorophenyl)tetrahydro-5-(1H-1,2,4-triazol-1-ylmethyl)-3 furanyl]methoxy]phenyl]-1-piperazinyl]phenyl]-2-[(1S,2S)-1-ethyl-2-hydroxypropyl]-2,4-dihydro-3H-1,2,4-triazol-3-one compound of formula-1, which comprising of:
  a) Reacting the 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one with Pd/C under hydrogen pressure in presence of hydrochloric acid in methanol,
  b) filtering the reaction mixture and adding acetone to the filtrate,
  c) cooling the reaction mixture and adjusting the pH of the reaction mixture,
  d) adding water to the reaction mixture,
  e) filtering the precipitated solid,
  f) adding acetone to the solid, obtained in step-(e) and heating the reaction mixture,
  g) filtering the reaction mixture,
  h) adding water to the filtrate and stirring the reaction mixture,
  i) filtering the precipitated solid,
  j) optionally, purifying the obtained solid in step-(i),
  k) adding dichloromethane to the solid, l) slowly adding the mixture obtained in step-(k) to n-pentane, m) stirring the reaction mixture, n) filtering the solid and then drying to get amorphous form of compound of formula-1.

Figure 3:
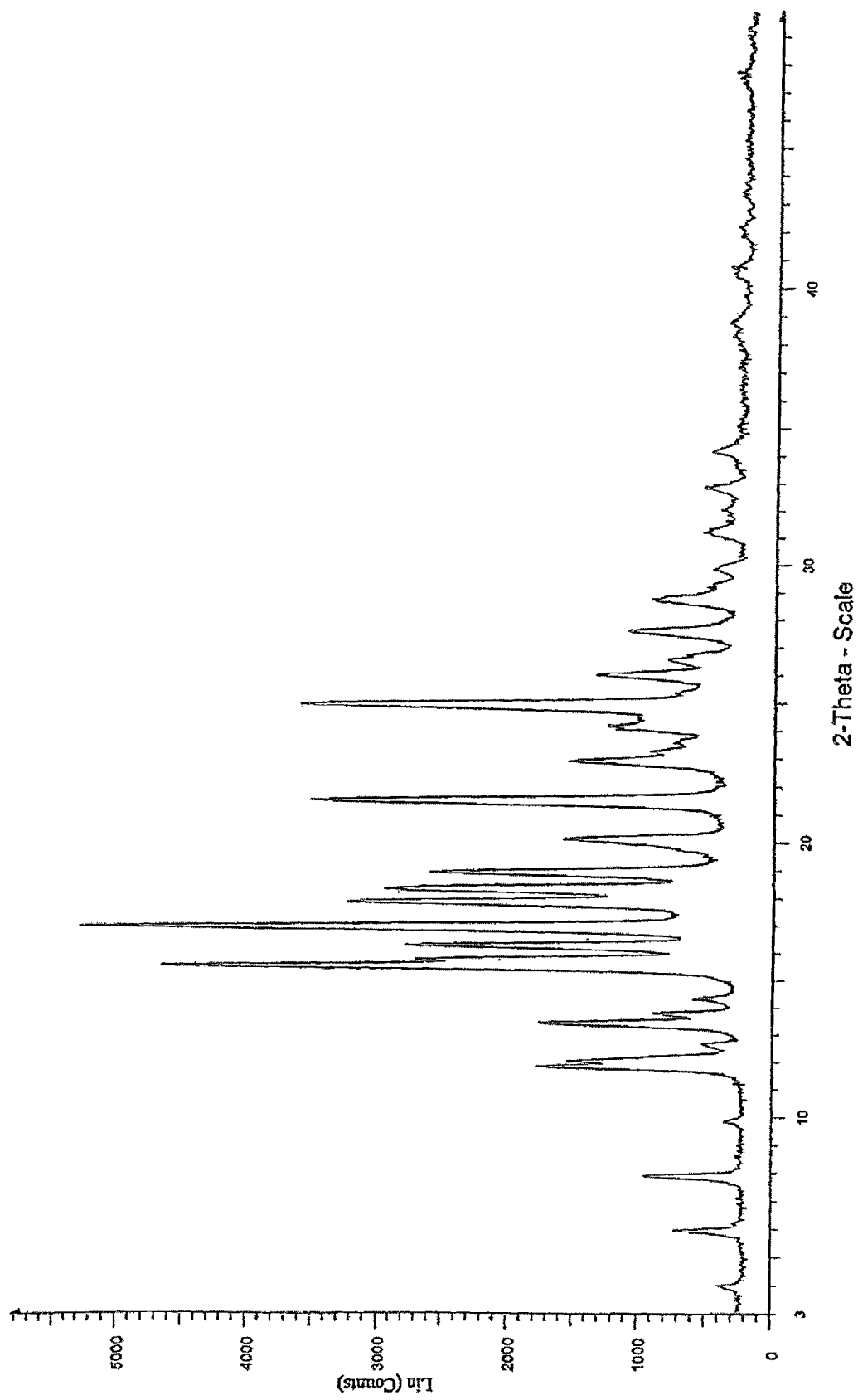
FIG. 3: Illustrates the PXRD pattern of crystalline form-M of benzylated posaconazole compound of formula-21.

The fourteenth aspect of the present invention is to provide a crystalline form-M of benzylated posaconazole, which is characterized by its powder X-ray diffractogram having peaks at about 3.90, 5.86, 7.82, 9.82, 11.79, 13.74, 16.24, 16.95, 17.83, 18.90, 20.09, 21.49, 22.89, 24.93 and 25.99±0.2 degrees two-theta as illustrated in figure-3.

The present invention involves the reaction of 1-((2S,3S)-2-(benzyloxy)pentan-3-yl)-4-(4-(4-(4-hydroxyphenyl)piperazin-1-yl)phenyl)-1H-1,2,4-triazol-5(4H)-one compound of formula-20 with ((3S,5R)-5-((1H-1,2,4-triazol-1-yl)methyl)-5-(2,4-difluorophenyl)tetrahydrofuran-3-yl)methyl-4-methylbenzenesulfonate compound of formula-10 in the presence of dimethylsulfoxide and, sodium hydroxide to provide crude benzylated posaconazole. The obtained crude benzylated posaconazole is isolated from isopropanol to provide pure crystalline form-M of benzylated posaconazole compound of formula-21 having HPLC purity greater than 99.85%.

WO2011/158248 A2 claims benzylated posaconazole as crystalline form-A, which is characterized by its powder X-ray diffractogram having peaks at about 2.04, 6.1, 12.24, 15.06, 15.73, 17.17, 17.37, 18.15, 19.42, 19.97, 24.34, 26.0. Whereas, the present invention provides a new crystalline form of benzylated posaconazole compound of formula-21 herein designated as crystalline form-M. The PXRD of the obtained crystalline compound of the present invention varies from the above said form-A, which is characterized by its powder X-ray diffractogram having peaks at about 3.90, 5.86, 7.82, 9.82, 11.79, 12.59, 13.38, 13.74, 16.24, 16.95, 17.83, 18.90, 20.09, 21.49, 22.89, 24.93, 26.53, 27.56, 28.73, 29.88 and 34.20.

The above said crystalline form-M of benzylated posaconazole compound of formula-21 is useful in the preparation of pure crystalline form-S, form-N, Form-I, IPA solvate and also amorphous compound of formula-1.

Figure 4:
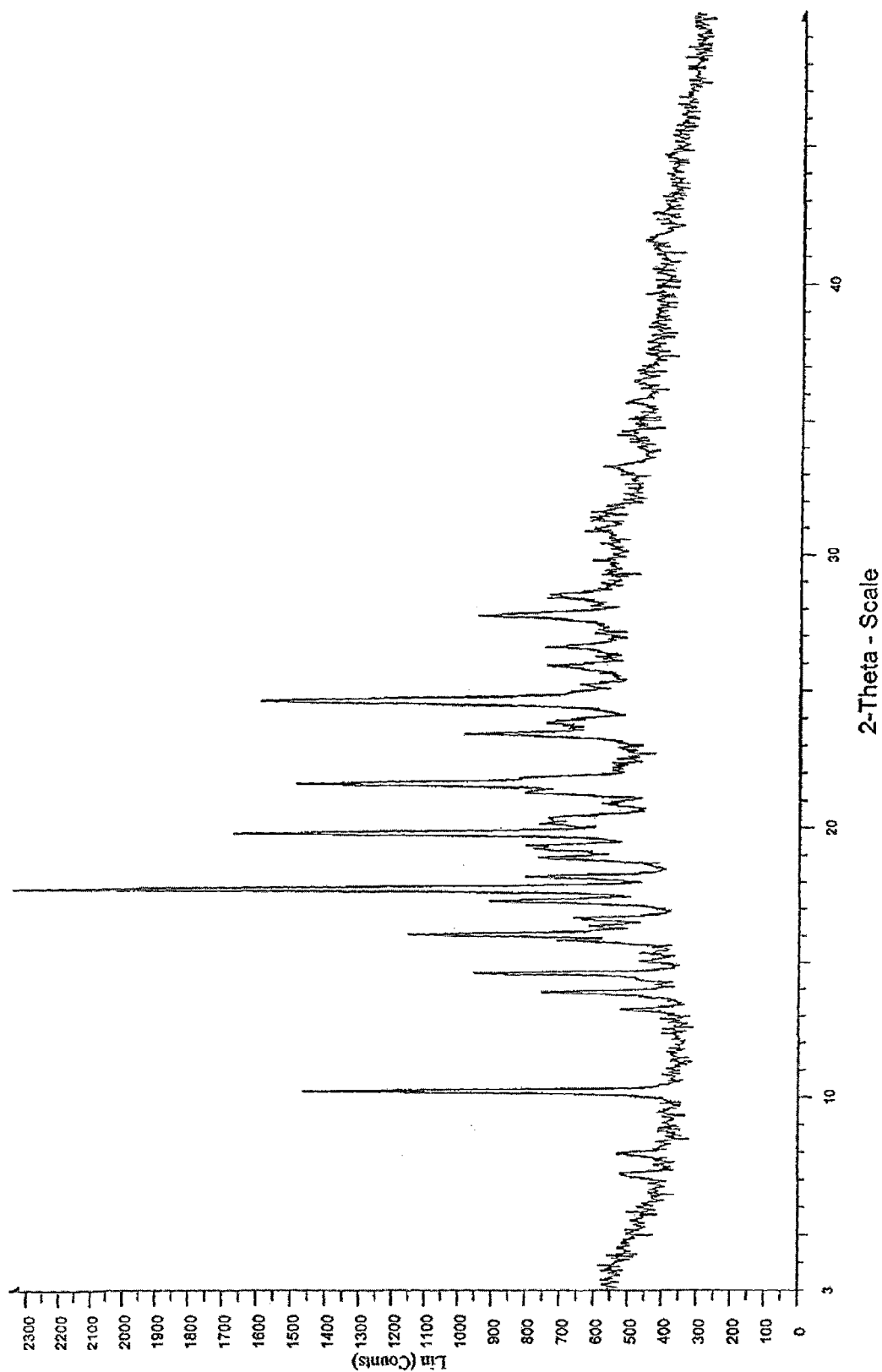
FIG. 4: Illustrates the PXRD pattern of crystalline form-S of posaconazole compound of formula-1 obtained as per the example-21.

The fifteenth aspect of the present invention is to provide novel crystalline form-S of triazole antifungal compound of formula-1 which is characterized by its powder X-ray diffractogram having peaks at about 7.19, 7.95, 10.20, 13.91, 15.38, 16.05, 16.69, 17.32, 17.77, 18.95, 19.29, 19.83, 20.20, 21.32, 21.67, 23.44, 24.70, 25.93, 26.64 and 27.79±0.2 degrees two-theta as illustrated in figure-4.

The sixteenth aspect of the present invention is to provide a process for the preparation of crystalline form-S of triazole antifungal compound of formula-1, comprising of:

a) Debenzylating the compound of formula-21 with Pd/C under hydrogen pressure in the presence of mineral acid in a suitable alcoholic solvent, b) filtering the reaction mixture, c) adding suitable organic solvent to the reaction mixture, d) cooling the reaction mixture to 10 to 15° C., e) adjusting pH of the reaction mixture, f) isolating the solid by adding purified water to the reaction mixture, g) stirring the reaction mixture, h) filtering the solid and washing with purified water to get the crystalline form-S of compound of formula-1.

Wherein;

in step-a) the suitable mineral acid is inorganic acid selected from hydrochloric acid, hydrobromic acid, hydroiodic acid and sulfuric acid, preferably hydrochloric acid; and suitable alcoholic solvent is selected from methanol, ethanol, isopropanol, preferably methanol.

in step-c) the suitable organic solvent selected from ketone solvent, ether solvent, ester solvent and chloro solvent, preferably ketone solvent.

The above said crystalline form-S of triazole antifungal compound of formula-1 is useful in the preparation of highly pure crystalline form-N, Form-I and also amorphous compound of formula-1.

The seventeenth aspect of the present invention is to provide novel crystalline form-N of triazole antifungal compound of formula-1 which is characterized by its powder X-ray diffractogram having peaks at about 7.92, 10.17, 10.86, 11.26, 12.98, 13.86, 17.72, 18.66, 22.62, 24.65, 25.84 and 28.52±0.2 degrees two-theta as illustrated in figure-5.

The eighteenth aspect of the present invention is to provide a process for the preparation of crystalline form-N of triazole antifungal compound of formula-1, comprising of;

a) Dissolving the compound of formula-1 in acetone, b) heating the reaction mixture to reflux, c) filtering the reaction mixture, d) adding purified water to the filtrate, e) stirring the reaction mixture, f) filtering the solid and washing with purified water to get crystalline form-N of compound of formula-1.

The above said crystalline form-N of triazole antifungal compound of formula-1 is useful in the preparation of crystalline IPA solvate, Form-I as well as amorphous triazole antifungal compound of formula-1.

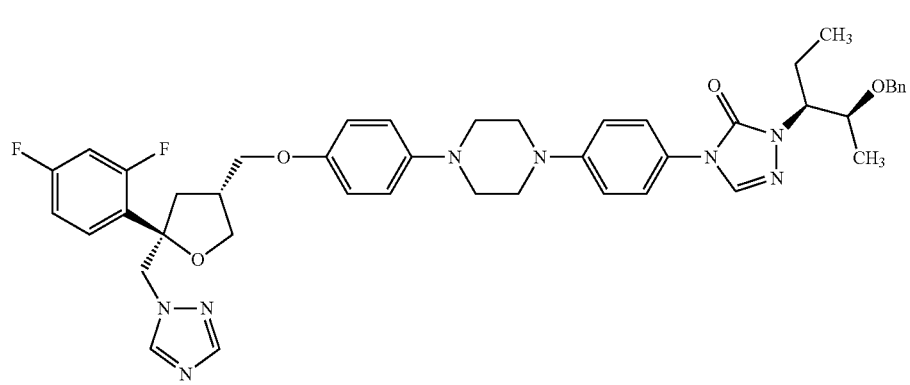

Formula-21

The above crystalline form-S, Form-N, Form-I, IPA solvate and amorphous forms of posaconazole can be prepared by using posaconazole compound of formula-1 as a starting material which is prepared by the known processes in the art or from the process disclosed in the above said aspects of the present invention.

Posaconazole produced by the present invention can be further micronized or milled to get the desired particle size to achieve desired solubility profile based on different forms of pharmaceutical composition requirements. Techniques that may be used for particle size reduction include, but not limited to ball, roller and hammer mills, and jet mills. Milling or micronization may be performed before drying, or after the completion of drying of the product.

Method of Analysis for Posaconazole Intermediates:

Related substances of the Posaconazole intermediates were analyzed by HPLC using the following conditions:

(R)-3-((S)-4-(2,4-difluorophenyl)-2-(hydroxymethyl)pent-4-enoyl)-4-phenyl oxazolidin-2-one (Formula-5)

Apparatus: A liquid chromatographic system is to be equipped with variable wavelength UV-detector; Column: kromosil-C18 125×4.6 mm, 3 μm, 5 μm or equivalent; Flow rate: 1.0 ml/min; Wavelength: 210 nm; Column Temperature: 25° C.; Injection volume: 10 μL; Run time: 45 min; Diluent: Water: Acetonitrile (1:1) v/v; Needle wash: Diluent; Elution: Gradient; Mobile phase-A: Buffer (100%); Mobile phase-B: Acetonitrile:water (90:10) v/v; Buffer: 1 ml of ortho phosphoric acid in 1000 ml of Milli-Q-water, mix well and filter through 0.22 μm Nylon membrane filter paper.

(R)-3-((3S,5R)-5-(2,4-difluorophenyl)-5-(iodomethyl)tetrahydrofuran-3-carbonyl)-4-phenyloxazolidin-2-one (Formula-6)

Apparatus: A liquid chromatographic system is to be equipped with variable wavelength UV-detector; Column: Chiral pak-IC 250×4.6 mm, 3 μm, 5 μm; Flow rate: 1.0 ml/min; Wavelength: 210 nm; Column Temperature: 25° C.; Injection volume: 10 μL; Run time: 40 min; Diluent: n-Hexane: IPA: THF (80:20:1) v/v; Needle wash: Diluent; Elution: Gradient; Mobile phase-A: n-Hexane: IPA: THF (90:10:1); Mobile phase-B: Isopropyl alcohol (100%).

(3S,5R)-5-(2,4-difluorophenyl)-5-(iodomethyl)tetrahydrofuran-3-carboxylic acid (Formula-7)

Apparatus: A liquid chromatographic system is to be equipped with variable wavelength UV-detector; Column: kromosil-C18 125×4.6 mm, 3 μm, 5 μm or equivalent; Flow rate: 1.0 ml/min; Wavelength: 210 nm; Column Temperature: 25° C.; Injection volume: 10 μL; Run time: 45 min; Diluent: Acetonitrile:Water (50:50) v/v; Needle wash: Diluent; Elution: Gradient; Mobile phase-A: Buffer (100%); Mobile phase-B: Acetonitrile: Water (90:10%) v/v; Buffer: 1 ml of ortho phosphoric acid in (85%) 1000 ml of Milli-Q-water and filter through 0.45 μm Nylon membrane filter paper.

(S)-1-phenylethanamine (S)-2-(benzyloxy)propanoic acid (Formula-13a)

Apparatus: A liquid chromatographic system is to be equipped with variable wavelength UV-detector; Column: chiral cel-OD-H 250×4.6 mm, 5 μm; Flow rate: 1.0 ml/min; Wavelength: 210 nm; Column Temperature: 35° C.; Injection volume: 10 μL; Run time: 35 min; Diluent: Mobile phase; Needle wash: Diluent; Elution: Isocratic; Mobile phase: A mixture of 20 ml of ethanol, 980 ml of n-hexane and 1.0 ml of trifluoro acetic acid.

(S)—N'-(2-(benzyloxy)propylidene)formylhydrazide (Formula-16)

Apparatus: A liquid chromatographic system is to be equipped with variable wavelength UV-detector; Column: chiralpak-IC, 250×4.6 mm, 5 μm; Flow rate: 0.8 ml/min; Wavelength: 220 nm; Column Temperature: 35° C.; Injection volume: 5 μL; Run time: 25 min; Diluent: n-hexane:Ethanol (90:10) v/v; Needle wash: Diluent; Elution: Isocratic; Mobile phase: A mixture of 100 ml of ethanol, 900 ml of n-hexane and 1.0 ml of trifluoro acetic acid.

HPLC Method of Analysis for Posaconazole:

Posaconazole is analyzed by HPLC using the following conditions: Apparatus: A liquid chromatographic system is to be equipped with variable wavelength UV-detector; Column: Grace Alltima C18,150×4.6 mm 3 μm or equivalent; Flow rate: 1.0 ml/min; Wavelength: 210 nm; Column Temperature: 28° C.; Injection volume: 10 μL; Run time: 60 min; Diluent: Acetonitrile: water (50:50 v/v); Needle wash: Acetonitrile: water (50:50 v/v); Elution: Gradient; Mobile phase-A: Buffer Acetonitrile (90:10) v/v; Mobile phase-B: Acetonitrile: water (90:10) v/v; Buffer: 1.74 grams of potassium hydrogen phosphate in 1000 ml of water. Adjust pH to 6.5 with diluted orthophosphoric acid and filtered through 0.45 μm Nylon membrane filter paper and sonicate to degas it.

PSD Method of Analysis for Posaconazole:

The particle size distribution of posaconazole compound of formual-1 is measured using the following conditions:

Instrument: Malvern Master sizer 2000; Measuring range: 0.02 to 2000 μm; Wet sample: Hydro 2000S; Dispersant: Water; Absorption Index: 0; Refractive Index of water: 1.330; Refractive Index of particle: 1.500; Stirrer speed: 2500 rpm; Obscuration range: 10-20%; Sensitivity: Normal; Measurement time: 12 seconds; Background time: 12 seconds; Internal sonication: 3 minutes; (Tip displacement-70%); Measurement repeat: 3 times at zero second interval.

HPLC Method of Analysis for Benzylated Posaconazole:

Benzylated posaconazole is analyzed by HPLC using the following conditions: Apparatus: A liquid chromatographic system is to be equipped with variable wavelength UV-detector; Column: X-bridge C18, 50×4.6 mm, 3.5 m (or) equivalent; Flow rate: 0.8 ml/min; Wavelength: 210 nm; Column Temperature: 40° C.; Injection volume: 5 μL; Run time: 35 min; Diluent: Water: Acetonitrile (40:60) v/v; Needle wash: Water: Acetonitrile (40:60) v/v; Elution: Gradient; Mobile phase-A: Buffer Acetonitrile (90:10) v/v; Mobile phase-B: Acetonitrile: water (90:10) v/v; Buffer: 1.74 grams of potassium hydrogen phosphate dibasic (anhydrous) in 1000 ml of Milli-Q-Water. Adjust its pH to 6.5 with diluted orthophosphoric acid and filtered through 0.22 μm Nylon membrane filter paper and sonicate to degas it.

PXRD analysis of crystalline triazole antifungal compound of formula-1 was carried out using BRUKER/AXS X-Ray diffractometer using Cu Kα radiation of wavelength 1.5406 A° and continuous scan speed of 0.03°/min.

RS/OVI analysis of amorphous posaconazole is carried out on Agilent GC-6850 series-2 with Flame Ionization detector, column AP vac, flow 2 psi and load is 1 μl, detector temperature is 260° C. and carrier gas is helium.

The process of the present invention is schematically represented as below:

Scheme-I
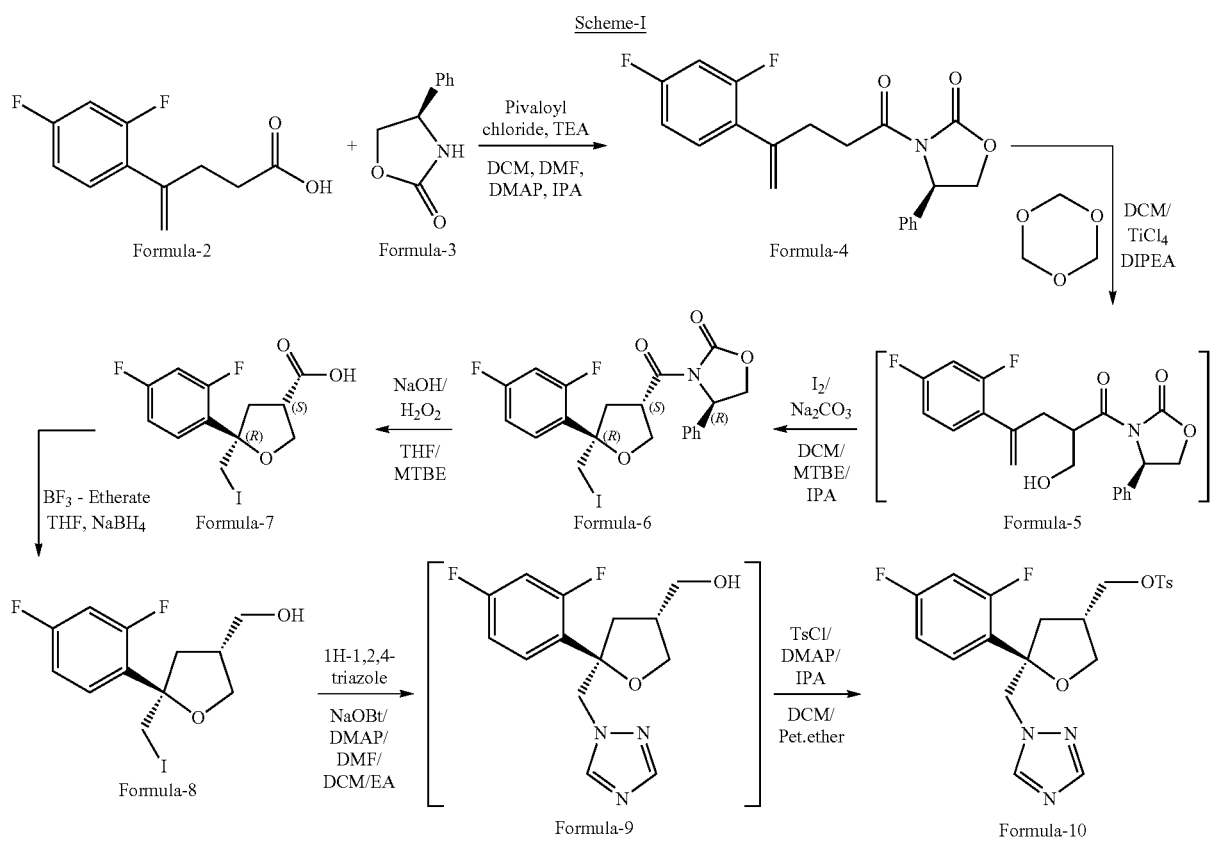
Scheme-II:
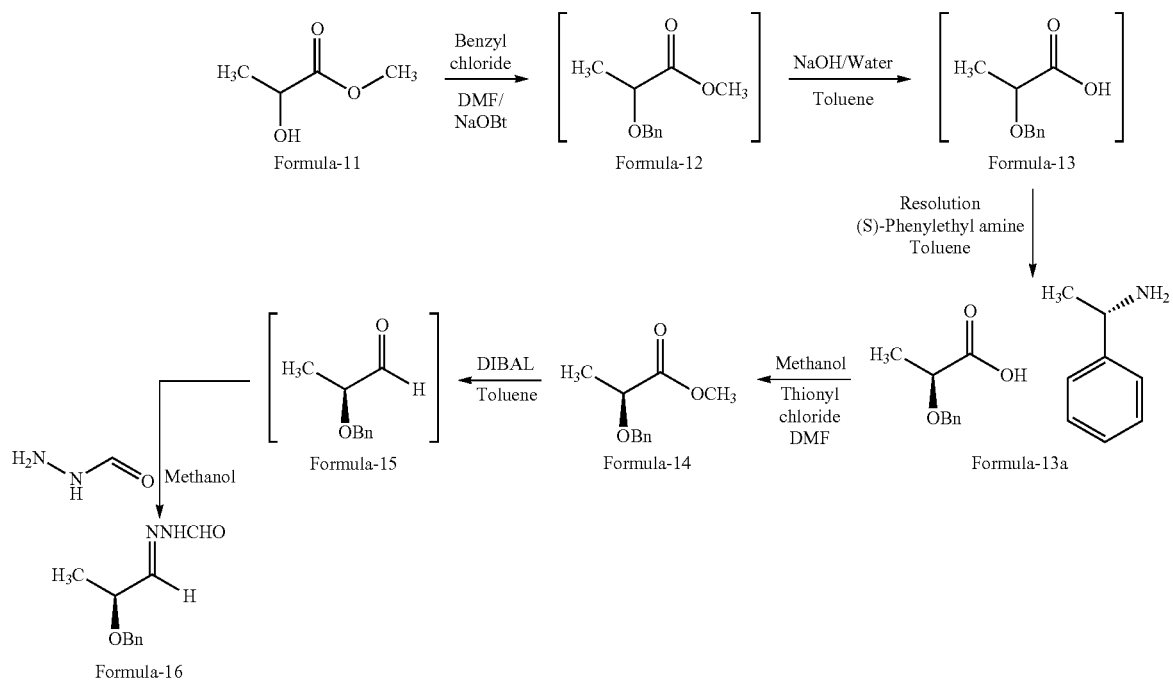

Scheme III:
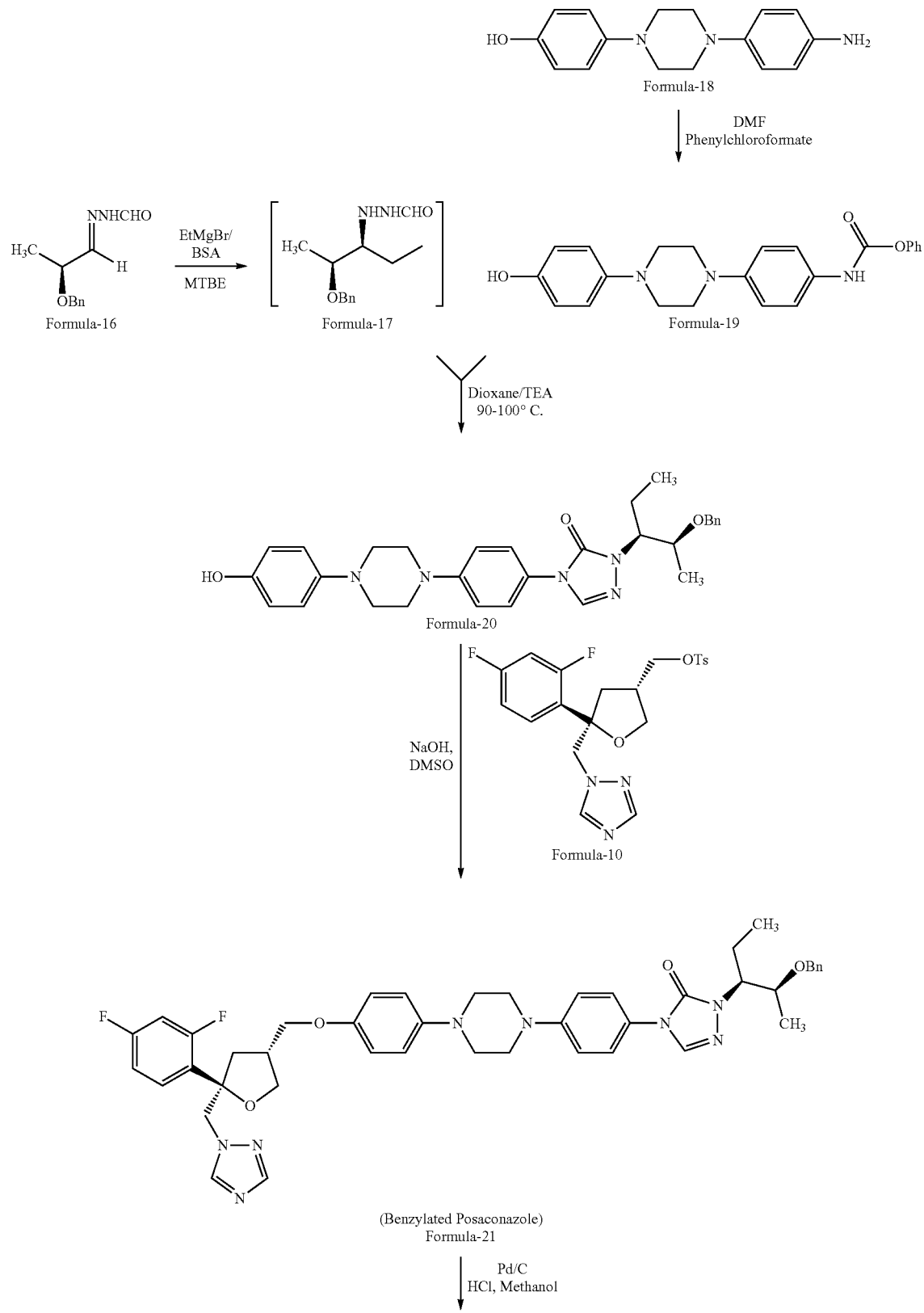

-continued

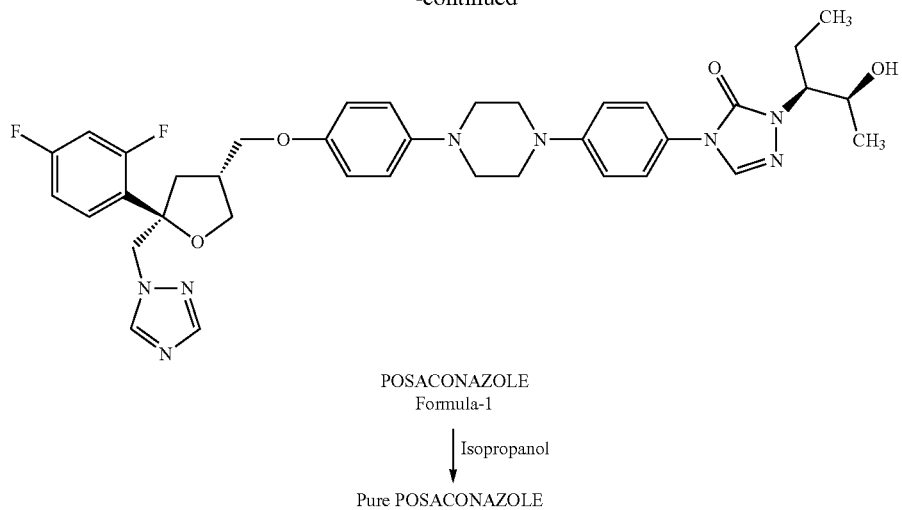

POSACONAZOLE
Formula-1

↓ Isopropanol

Pure POSACONAZOLE

The process described in the present invention was demonstrated in examples illustrated below. These examples are provided as illustration only and therefore should not be construed as limitation of the scope of the invention.

Example-1

Preparation of 4-(2,4-difluorophenyl)pent-4-enoic acid (Formula-2)

To a mixture of 4-(2,4-difluorophenyl)-4-oxobutanoic acid (100 g) and toluene (1000 ml), added methyl triphenylphosphine iodide (377.5 g) and sodium tertiary butoxide (183 g) at 25-30° C. Heated the reaction mixture to 50-55° C. and stirred for 6-8 hours at the same temperature. After completion of the reaction, cooled the reaction mixture to 25-30° C. Water was added to the reaction mixture and both organic and aqueous layers were separated. pH of aqueous layer was adjusted to 11 using 50% hydrochloric acid. Extracted the aqueous layer with toluene and washed the aqueous layer with dichloromethane. pH of the aqueous layer was further adjusted to 2.5 using 50% HCl and the reaction mixture was stirred for 45 minutes. Filtered the obtained solid, washed with water and then dried to get the title compound. Cyclohexane (500 ml) was added to the obtained solid and heated to 45-50° C. Carbon (10 g) was added to the reaction mixture and stirred for 15 minutes. Filtered the reaction mixture and washed with hot cyclohexane. Distilled off half of the solvent under reduced pressure. Cooled the reaction mixture to 10-15° C. and stirred for 60 minutes at the same temperature. Filtered the solid and washed with chilled cyclohexane and dried to get the title compound. Yield: 65.75 g Example-2

Preparation of (R)-3-(4-(2,4-difluorophenyl)pent-4-enoyl)-4-phenyl oxazolidin-2-one (Formula-4)

To a solution of 4-(2,4-difluorophenyl)pent-4-enoic acid compound of formula-2 (100 g) in dichloromethane (800 ml), added triethylamine (97.4 g) at 25-30° C. and the reaction mixture was stirred for 15 minutes at the same temperature. The reaction mixture was cooled to 10-15° C. and added pivaloyl chloride (63 g) to the reaction mixture over a period of 45 minutes. Temperature of the reaction mixture was raised to 25-30° C. and the reaction mixture was stirred for 2 hours at 25-30° C. After completion of the reaction, added (R)-4-phenyloxazolidin-2-one compound of formula-3 (69 g), 4-dimethylamino pyridine (21 g), dimethyl formamide (37 ml) and followed by dichloromethane (200 ml) to the above reaction mixture. Heated the reaction mixture to 45° C. and stirred for 2 hours at the same temperature. After completion of the reaction, the reaction mixture was cooled to 25-30° C. Sulfuric acid was added to the reaction mixture and stirred for 15 minutes. Both organic and aqueous layers were separated and the organic layer was washed with water. Distilled off the solvent completely from the organic layer under reduced pressure and isopropyl alcohol was added to the obtained residue at 25-30° C. and stirred for 15 minutes at the same temperature. The reaction mixture was cooled to 0-10° C. and then stirred for 1½ hour at the same temperature. Filtered the obtained solid, washed with chilled isopropyl alcohol and then dried to get title compound.
Yield: 95 g; purity by HPLC: 98.24%, 0.17% (R-POZ), 0.73% (SMI); Melting range: 50-55° C.

Example-3

Preparation of (R)-3-((3S,5R)-5-(2,4-difluorophenyl)-5-(iodomethyl) tetrahydrofuran-3-carbonyl)-4-phenyloxazolidin-2-one (Formula-6)

Step-a): Preparation of (R)-3-((S)-4-(2,4-difluorophenyl)-2-(hydroxymethyl) pent-4-enoyl)-4-phenyloxazolidin-2-one (Formula-5)

Titanium chloride solution (prepared from 33.8 ml of titanium chloride and 50 ml of dichloromethane) was added to a pre-cooled solution of (R)-3-(4-(2,4-difluorophenyl)pent-4-enoyl)-4-phenyloxazolidin-2-one compound of formula-4 (100 g) in dichloro methane (1000 ml) at −20 to −10° C. under nitrogen atmosphere and diisopropyl ethylamine (45.61 μm) was added to the reaction mixture and stirred for 40 minutes at −20 to −10° C. A trioxane solution (prepared from 52.94 g of trioxane and 150 ml of dichloro methane) was added to the reaction mixture at −20 to −10° C. and followed by titanium chloride solution (prepared from 33.8 ml of titanium chloride and 50 ml of dichloro methane) at −20 to −10° C. Temperature of the reaction mixture was raised to −5 to 0° C. and stirred for 2 hours at −5 to 0° C. After completion of the reaction, the reaction mixture was added to 10% ammonium chloride at 10-15° C. Both organic and aqueous layers were separated and the aqueous layer was extracted with dichloro methane. Both the dichloro methane layers were combined and washed with water followed by 10% sodium chloride solution. The obtained dichloro methane layer was taken to the next step without isolating the title compound.

Step-b): Preparation of (R)-3-((3S,5R)-5-(2,4-difluorophenyl)-5-(iodomethyl)tetra hydrofuran-3-carbonyl)-4-phenyloxazolidin-2-one (Formula-6)

To the above obtained dichloromethane layer containing (R)-3-((S)-4-(2,4-difluoro phenyl)-2-(hydroxymethyl)pent-4-enoyl)-4-phenyloxazolidin-2-one compound of formula-5, added sodium carbonate (59.4 g) followed by iodine (177.8 g) and the reaction mixture was stirred for 3 hours at 25-35° C. After completion of the reaction, the reaction mixture was quenched with 30% hypo solution and the reaction mixture was extracted with methyl tertiary butyl ether. Both organic and aqueous layers were separated and the organic layer was washed with 30% hypo solution, followed by 10% sodium chloride solution. Distilled off the solvent completely from the organic layer. Isopropanol (600 ml) was added to the obtained compound and the reaction mixture was stirred for 1½ hour at 25-30° C. Filtered the solid, washed with isopropyl alcohol and then dried to get the title compound. Yield: 65 g; Chiral purity: 99.5%

Example-4

Preparation of (R)-3-((S)-4-(2,4-difluorophenyl)-2-(hydroxymethyl) pent-4-enoyl)-4-phenyloxazolidin-2-one (Formula-5)

Titanium chloride (prepared from 33.8 ml of titanium chloride and 50 ml of dichloromethane) solution (prepared from 33.8 ml of titanium chloride and 50 ml of dichloromethane) was added to a pre-cooled solution of compound of formula-4 (100 g) in dichloro methane (1000 ml) at −20 to −10° C. under nitrogen atmosphere and Diisopropyl ethylamine (45.61 μm) was added to the reaction mixture and was stirred for 40 minutes at −20 to −10° C. A trioxane (prepared from 52.94 g of trioxane and 150 ml of dichloro methane) solution was added to the reaction mixture over a period of 45 minutes at −20 to −10° C. and followed by titanium chloride solution over a period of 45 minutes at −20 to −10° C. Temperature of the reaction mixture was raised to −5 to 0° C. and stirred for 2 hours at −5 to 0° C. After completion of the reaction, added ammonium chloride solution and separated both the aqueous and organic layers. Distilled off the solvent from organic layer to obtain a residue. Isopropyl alcohol was added to the obtained residue and stirred for 3 hours at 25-30° C. Filtered the solid and washed with isopropyl alcohol. Dried the solid to get the title compound. Yield: 81 g.

Example-5

Preparation of (3S,5R)-5-(2,4-difluorophenyl)-5-(iodomethyl)tetrahydro furan-3-carboxylic acid (Formula-7)

Sodium hydroxide solution (prepared from 17.7 g of sodium hydroxide and 390 ml of water) was added to a pre-cooled solution of hydrogen peroxide (30 ml), water (65 ml) and tetrahydrofuran (390 ml) at 0-10° C., followed by a solution of (R)-3-((3S,5R)-5-(2,4-difluorophenyl)-5-(iodomethyl)tetrahydrofuran-3-carbonyl)-4-phenyloxazolidin-2-one compound of formula-6 (130 g) in tetrahydrofuran (390 ml) at 0-10° C. and the reaction mixture was stirred for 30 minutes at 0-10° C. Further temperature of the reaction mixture was raised to 25-30° C. and then stirred for 2 hours at 25-30° C. After completion of the reaction, the reaction mixture was quenched with 10% sodium sulphite solution and the reaction mixture was washed with toluene. The pH of aqueous layer was adjusted to 10.5 using 50% HCl and then washed with dichloromethane. Further pH of aqueous layer was again adjusted to 4.5 using 50% HCl. The aqueous layer was extracted with methyl tertiary butyl ether and distilled off the solvent from methyl tert.butyl ether layer and then co-distilled with cyclohexane. Cyclohexane (190 ml) was added to the obtained compound and stirred for 2 hours at 25-30° C. Filtered the solid, washed with cyclohexane and then dried to get title compound. Yield: 65 g; MR: 80-87° C.

Example-6

Preparation of ((3R,5R)-5-(2,4-difluorophenyl)-5-(iodomethyl) tetrahydrofuran-3-yl)methanol (Formula-8)

A solution of (3S,5R)-5-(2,4-difluorophenyl)-5-(iodomethyl)tetrahydrofuran-3-carboxylic acid compound of formula-7 (150 g) in tetrahydrofuran (750 ml) was added to a pre-cooled solution of sodium borohydride (45.2 g) in tetrahydrofuran (750 ml) at 0-5° C., followed by BF3-etherate (172.29 g) at 0-5° C. Temperature of the reaction mixture was raised to 25-30° C. and stirred for 2 hours at the same temperature. After completion of the reaction, the reaction mixture was quenched with 5% aqueous hydrochloric acid. Added ethylacetate to the reaction mixture. Both organic and aqueous layers were separated and the aqueous layers were extracted with ethyl acetate. Both the organic layers were combined, washed with water followed by 10% sodium chloride solution and then distilled off the solvent to get the title compound as a residue. Yield: 140 g; purity by HPLC: 98.5%.

Example-7

Preparation of ((3S,5R)-5-((1H-1,2,4-triazol-1-yl)methyl)-5-(2,4-difluoro phenyl)tetrahydrofuran-3-yl) methyl 4-methylbenzenesulfonate (Formula-10)

Step-a): Preparation of ((3R,5R)-5-((1H-1,2,4-triazol-1-yl)methyl)-5-(2,4-difluoro phenyl)tetrahydrofuran-3-yl)methanol (Formula-9)

Added 4-dimethylaminopyridine (8.61 g) and sodium tertiary butoxide (339 g) to a mixture of dimethylformamide (2500 ml) and 1,2,4-triazole (243.6 g) and stirred the reaction mixture for 30-45 minutes at 25-35° C. ((3R,5R)-5-(2,4-difluorophenyl)-5-(iodomethyl)tetrahydrofuran-3-yl)methanol compound of formula-8 (250 g) was added to the reaction mixture. The reaction mixture was heated to 100-110° C. and stirred for 18 hours at the same temperature. After completion of the reaction, the reaction mixture was cooled to 25-35° C. and then poured into water. Added dichloromethane to the reaction mixture. Both organic and aqueous layers were separated and the aqueous layer was extracted with dichloro methane. The combined dichloromethane layers were extracted with 50% aqueous HCl and separating both the aqueous and organic layers then pH of the aq. layer was adjusted to 8-9 with 50% aqueous sodium hydroxide. Both organic and aqueous layers were separated and the aqueous layer was extracted with ethyl acetate. The ethyl acetate layer was washed with water followed by sodium chloride solution and then distilled to get title compound as a residue. The obtained residue containing the title compound of formula-9 was taken to next step without isolation.

Step-b): Preparation of ((3S,5R)-5-((1H-1,2,4-triazol-1-yl)methyl)-5-(2,4-difluoro phenyl)tetrahydrofuran-3-yl)methyl 4-methylbenzenesulfonate (Formula-10)

Dichloromethane (1250 ml) was added to the obtained residue obtained in step-a) at 25-30° C. and the reaction mixture was cooled to 0-5° C. Dimethylamino pyridine (8.61 g) was added to the reaction mixture, and followed by p-toluene sulfonyl chloride (121.1 g) at 0-5° C. and stirred the reaction mixture for 1 hour at 0-5° C. Temperature of the reaction mixture was raised to 25-30° C. and stirred for 10 hours at 25-30° C. After completion of the reaction, the reaction mixture was quenched with water. Both the organic and aqueous layers are separated. Extracted the aqueous layer with dichloromethane and washed the dichloromethane layer with water followed by 10% sodium chloride solution. Distilled off the solvent completely from dichloromethane layer to get the crude title compound. To the obtained compound pet.ether (625 ml) and followed by isopropyl alcohol (62.5 ml) were added and the reaction mixture was stirred for 2 hours at 25-30° C. Filtered the precipitated solid. The obtained solid was recrystallized using isopropyl alcohol (625 ml) followed by carbon to get pure title compound.
Yield: 75 grams; purity by HPLC: 98.5%.

The above prepared compound of formula-10 can be used as a key intermediate in the preparation of Triazole Antifungal drug, preferably in posaconazole.

Example-8

Preparation of Phenyl-4-(4-(4-hydroxyphenyl)piperazin-1-yl)phenyl carbamate (Formula-19)

Phenyl chloroformate (139.5 g) was added to a pre-cooled solution of 4-(4-(4-aminophenyl)piperazin-1-yl)phenol compound of formula-18 (200 g) in dimethyl formamide (1400 ml) at 0-10° C. Temperature of the reaction mixture was raised to 25-30° C. and then stirred for 3 hours at 25-30° C. After completion of the reaction, the reaction mixture was quenched with water. Filtered the precipitated solid and washed with water. Isopropyl alcohol (600 ml) was added to the solid and the reaction mixture was heated to 60-65° C. and stirred for 1 hour at the same temperature. Further the reaction mixture was cooled to 25-30° C. and then stirred for 1 hour at 25-30° C. Filtered the solid, washed with IPA and then dried to get title compound.
Yield: 215 g; Purity by HPLC: 95%

Example-9

Preparation of (S)-1-phenylethanamine salt of (S)-2-(benzyloxy) propanoic acid (Formula-13a)

a) Preparation of methyl 2-(benzyloxy)propanoate (Formula-12)

To a pre-cooled solution of potassium tertiary butoxide (538.4 g) in DMF (1750 ml) at −20 to −10° C., added racemic methyl lactate compound of formula-11 (500 g) followed by benzyl chloride (547 g) at −20 to −10° C. and the reaction mixture was stirred for 5 hours at the same temperature. After completion of the reaction, the reaction mixture was quenched with water and the reaction mixture was extracted with ethyl acetate. The ethyl acetate layer was washed with water and 10% sodium chloride solution and then distilled off the solvent from ethyl acetate layer under reduced pressure to get the title compound as a residue. The obtained residue was taken into next step without isolation.

b) Preparation of 2-(benzyloxy)propanoic acid (Formula-13)

A mixture of residue containing methyl 2-(benzyloxy)propanoate compound of formula-12 obtained in step-a) and water (500 ml) was cooled to 0-5° C. A solution of sodium hydroxide (51.5 g) in water (375 ml) was added to reaction mixture at 0-5° C. and stirred the reaction mixture for 1 hour at the same temperature. Temperature of the reaction mixture was raised to 25-30° C. and stirred for 4 hours at this temperature. After completion of the reaction, washed the reaction mixture with dichloromethane. Both dichloromethane and aqueous layers were separated and pH of aqueous layer was adjusted to 2.5 using 50% hydrochloric acid solution. Extracted the aqueous layer with dichloromethane. Distilled off the solvent from dichloromethane layer under reduced pressure to get the title compound as a residue. The obtained residue can be taken into next step without isolation.

c) Preparation of (S)-1-phenylethanamine salt of (S)-2-(benzyloxy)propanoic acid (Formula-13a)

(S)-1-phenyl ethyl amine (184.9 g) was added to a mixture of residue containing 2-(benzyloxy)propanoic acid obtained in the above step-b) and toluene (1375 ml) at 25-30° C. The reaction mixture was stirred for 6 hours at 25-30° C. Filtered the precipitated solid and washed with toluene and then dried to get the title compound. The obtained compound was recrystallized using toluene to get pure title compound.
Yield: 150 g; Chiral purity: 99.0%

Example-10

Alternative process for the preparation of (S)-1-phenylethanamine salt of (S)-2-(benzyloxy)propanoic acid (Formula-13a)

a) Preparation of methyl 2-(benzyloxy)propanoate (Formula-12)

To a pre-cooled solution of racemic methyl lactate (200 g) in dimethyl formamide (400 ml) at 0-10° C., added benzyl chloride (218.8 g). Sodium tertiary butoxide (224.6 g) was added to the reaction mixture at 0-10° C. and stirred for 6 hours at 25-35° C. After completion of the reaction, the reaction mixture was quenched with water and extracted with toluene. The toluene layer was washed with water followed by 10% sodium chloride solution. The obtained toluene layer containing title compound was taken to next step.

b) Preparation of 2-(benzyloxy)propanoic acid (Formula-13)

The toluene layer obtained in step-a) was cooled to 10-15° C. and was added to a pre-cooled solution of sodium hydroxide (prepared from 61.5 g of sodium hydroxide and 350 ml of water). Temperature of reaction mixture was raised to 25-35° C. and then stirred for 4 hours at 25-35° C. After completion of reaction separated the aqueous and organic layers, pH of aqueous layer was adjusted to 2.5 using 50% HCl. The aqueous layer was extracted with toluene and washed with 10% sodium chloride solution and water. The obtained toluene layer containing title compound was taken to next step.

c) Preparation of (S)-1-phenylethanamine salt of (S)-2-(benzyloxy)propanoic acid (Formula-13a)

(S)-1-phenyl ethyl amine (116.2 g) was added to the toluene layer obtained in step-b) at 25-30° C. and stirred the reaction mixture for 6 hours at 25-30° C. Filtered the precipitated solid and washed with toluene. The obtained solid was recrystallized using toluene to get pure title compound. Yield: 100 g; Chiral purity: 99.0%.

Example-11

Preparation of (S)-methyl 2-(benzyloxy)propanoate (Formula-14)

Dimethyl formamide (0.5 ml) was added to a mixture of (S)-1-phenylethanamine salt of (S)-2-(benzyloxy)propanoic acid compound of formula-13a obtained in step-c) of above examples-9 &. 10 (200 g) and methanol (600 ml) and the reaction mixture was cooled to 0-5° C. Thionyl chloride (58.4 ml) was slowly added to the reaction mixture at 0-5° C. over a period of 1 hour and stirred for 1 hour at 0-10° C. After completion of the reaction, the reaction mixture was quenched with water and extracted with dichloro methane. Both aqueous and dichloro methane layers were separated, dichloro methane layer was washed with 10% sodium chloride and water. Distilled off the solvent completely from dichloro methane layer to get title compound. Yield: 129 g; Chiral purity: 99.5%

Example-12

Preparation of (S)—N'-(2-(benzyloxy)propylidene) formohydrazide (Formula-16)

a) Preparation of Formyl Hydrazine

A solution of hydrazine hydrate (138 g) and water (20 ml) was added slowly to a mixture of ethyl formate (200 g) and methanol (200 ml) by cooling the reaction mixture to 0-10° C. The reaction mixture was heated to 55-60° C. and stirred for 24 hours at 55-60° C. Distilled off the solvent under reduced pressure. Isopropanol was added to the obtained residue. The reaction mixture was cooled to 0-5° C. and stirred for 2 hours at 0-5° C. Filtered the solid, washed with isopropyl alcohol and then dried to get title compound. Yield: 140 g b) Preparation of (S)-2-(benzyloxy)propanal (Formula-15)

A mixture of (S)-methyl 2-(benzyloxy)propanoate compound of formula-14 obtained in example-11 (100 g) and toluene (200 ml) was cooled to −75 to 70° C. under nitrogen atmosphere. DIBAL (500 ml) was added to the reaction mixture and stirred for 3 hours at the same temperature. After completion of the reaction, the reaction mixture was quenched with methanol and 30% hydrochloric acid was added to it at −75 to −70° C. Temperature of reaction mixture was raised to 25-30° C. Both organic and aqueous layers were separated and the aqueous layer was extracted with toluene. Both organic layers were combined, washed with 5% sodium bicarbonate and 10% sodium chloride solution. The organic layer containing title compound is carried for the next step without distillation.

c) Preparation of (S)—N'-(2-(benzyloxy)propylidene)formo hydrazide (Formula-16)

To a pre-cooled solution of formyl hydrazine (40.3 g) in methanol (290 ml) at 0-5° C., toluene layer containing (S)-2-(benzyloxy)propanal compound of formula-15 obtained in step-b) was added. Slowly raised the temperature of reaction mixture to 25-30° C. and stirred for 4 hours at 25-30° C. After completion of the reaction, distilled off the solvent under reduced pressure to get title compound. Ethyl acetate (210 ml) was added to the obtained compound and stirred for 1 hour at 25-30° C. Filtered the reaction mixture to remove the unwanted solid and washed with ethyl acetate. Distilled off the solvent completely from the filtrate under reduced pressure to get semi-solid. Petroleum ether (210 ml) was added to the obtained semi-solid and stirred for 2 hours at 25-30° C. Filtered the precipitated solid, washed with petroleum ether and then dried to get title compound.
Yield: 67 g; Chiral purity: 99.5%.

Example-13

Preparation of N'-((2S,3S)-2-(benzyloxy)pentan-3-yl)formohydrazide (Formula-17)

A mixture of methyl tertiary butyl ether (150 ml), Mg turnings (18 g) and $I_2$ (0.03 g) was heated to 40-45° C. under nitrogen atmosphere and ethyl bromide (81.8 g) was added slowly to the reaction mixture for about 1 hour. The reaction mixture was further heated to 50-55° C. and methyl tertiary butyl ether (60 ml) was added to it. The reaction mixture was stirred for 2 hours at 50-55° C. and cooled 0-10° C. N,O-Bistrimethyl silyl acetamide (60.9 g) was added to a mixture of methyl tertiary butyl ether (150 ml) and (S)—N'-(2-(benzyloxy)propylidene)formohydrazide compound of formula-16 (30 g) over a period of 45 minutes at 25-30° C. and stirred for 1 hour at 25-30° C. This reaction mixture was added to the above reaction mixture at 0-10° C. under nitrogen atmosphere. Temperature of the reaction mixture was raised to 25-30 C and stirred for 8 hours at 25-30° C. After completion of reaction, the reaction mixture was quenched with 8% acetic acid in chilled water. The reaction mixture was stirred for 30 minutes at 25-30° C. and both organic and aqueous layers were separated. The organic layer was washed with 10% sodium chloride solution and followed by water. Distilled off the solvent completely to get the title compound. The obtained compound was taken into next step without isolating the compound. Yield: 48 g Example-14

Preparation of 1-((2S,3S)-2-(benzyloxy)pentan-3-yl)-4-(4-(4-(4-hydroxyphenyl)piperazin-1-yl)phenyl)-1H-1,2,4-triazol-5(4H)-one (Formula-20)

a) Preparation of Compound of Formula-20

A mixture of N'-((2S,3S)-2-(benzyloxy)pentan-3-yl)formohydrazide compound of formula-17 (45.5 g) obtained in example-13, dioxane (500 ml) added phenyl 4-(4-(4-hydroxyphenyl)piperazin-1-yl)phenylcarbamate compound of formula-19 (50 g) was heated to 90-100° C. Triethylamine (26 g) was added to the reaction mixture at 90-100° C. over a period of 1 hour and stirred for 24 hours at 90-100° C. After completion of the reaction, the reaction mixture was cooled to 25-30° C. and dichloromethane was added to the reaction mixture. Filtered the reaction mixture through hyflow bed and washed with dichloromethane. Water was added to the filtrate. Both organic and aqueous layers were separated and the aqueous layer was extracted with dichloromethane. Both organic layers were combined and washed with 2% sodium hydroxide solution followed by water, and then with 5% hydrochloric acid solution followed by water and 5% $NaHCO_3$ solution washing. Distilled off the solvent from organic layer under reduced pressure to get the title compound. Isopropyl alcohol (75 ml) was added to the obtained compound and the reaction mixture was cooled to 25-30° C. The reaction mixture was stirred for 6 hours at 25-30° C. Filtered the solid, washed with isopropyl alcohol and then dried to get the title compound. Yield: 28 g; Purity by HPLC: 97.67%; Impurity-A: 0.37% b) Purification of Compound of Formula-20

The obtained compound of formula-20 (30 g) was dissolved in methanol (960 ml) by heating at 60-65° C. The reaction mixture was cooled to 25-30° C. and stirred for 30 minutes at the same temperature. Filtered the precipitated solid and dried to get the pure compound of formula-20. Yield: 70%; Purity by HPLC: 99.15%; Impurity-A: 0.09%

Example-15

4-(4-(4-(4-(((3R,5R)-5-((1H-1,2,4-triazol-1-yl)methyl)-5-(2,4-difluoro phenyl)tetrahydrofuran-3-yl)methoxy)phenyl)piperazin-1-yl)phenyl)-1-((2S,3S)-2-(benzyloxy)pentan-3-yl)-1H-1,2,4-triazol-5(4H)-one (Formula-21)

Added 1-((2S,3S)-2-(benzyloxy)pentan-3-yl)-4-(4-(4-(4-hydroxyphenyl) piperazin-1-yl)phenyl)-1H-1,2,4-triazol-5 (4H)-one compound of formula-20 (35 g) to a mixture of dimethylsulfoxide (350 ml) and sodium hydroxide (3.4 g) and water (7 ml) at 25-30° C. and stirred for 45 minutes at 25-30° C. ((3S,5R)-5-((1H-1,2,4-triazol-1-yl)methyl)-5-(2,4-difluorophenyl)tetrahydrofuran-3-yl)methyl-4-methylbenzenesulfonate compound of formula-10 (31.5 g) was added to the above reaction mixture at 25-30° C. and stirred 5 hours at 25-30° C. After completion of the reaction, water was added to the reaction mixture. The reaction mixture was extracted twice with ethyl acetate. The organic layers were washed with 10% sodium chloride solution. Distilled off the solvent under reduced pressure to get the compound as residue. Dissolved the obtained residue in isopropanol (320 ml) at 45-50° C. Filtered the solid, washed with water and dried to get the title compound. Yield: 98%; Purity by HPLC: 95.1%

Example-16

Preparation of Posaconazole (Formula-1)

5N hydrochloric acid (72 ml) and 10% Pd—C(10 g) were added to a solution of 4-(4-(4-(4-(((3R,5R)-5-((1H-1,2,4-triazol-1-yl)methyl)-5-(2,4-difluorophenyl)tetrahydro furan-3-yl)methoxy)phenyl)piperazin-1-yl)phenyl)-1-((2S,3R)-2-(benzyloxy)pentan-3-yl)-1H-1,2,4-triazol-5(4H)-one compound of formula-21 (42 g) in methanol (420 ml). The reaction mixture was hydrogenated for 5 hours under a hydrogen gas pressure of 4-5 kg/cm² at 50°. After completion of reaction, the catalyst was filtered off and washed with methanol. pH of the filtrate was adjusted to ~7.0 using 4N sodium hydroxide. Water was added to the reaction mixture and stirred for 2 hours at 25-35° C. Filtered the separated solid and washed with water. The obtained solid was dissolved in acetone (320 ml) and stirred at reflux temperature for 30 minutes. Filtered the undissolved product and added water to the filtrate and stirred the reaction mixture for 4 hours at 25-35° C. Filtered the separated solid and washed with water. Further the solid was recrystallized from isopropyl alcohol to get the title compound. Purity by HPLC: 99.85%; Yield: 75.0%: Chiral purity by HPLC: 99.82%.

Example-17

Preparation of Amorphous Posaconazole Compound of Formula-1

A mixture of Posaconazole (100 g) and dichloromethane (500 ml) was stirred to get clear solution. The solution was filtered and the filtrate was slowly added to n-pentane (7500 ml) at 25-30° C. The resulting mixture was stirred for 2 hours at the same temperature. The compound obtained was filtered and washed with n-pentane. Dried the obtained solid to get amorphous solid. Yield: 95%.

Particle size distribution: D(0.1): 11.69 μm; D(0.5): 52.74 μm; D(0.9): 116.52 μm.

Example-18

Preparation of Isopropanol Solvate Form of Posaconazole (Formula-1)

Dissolved the posaconazole (30 g) in isopropyl alcohol (300 ml) by heating to reflux temperature. Filtered the reaction mixture, filtrate was cooled to 25-30° C. and stirred for 2 hours at 25-30° C. Filtered the solid and washed with isopropyl alcohol. Dried the obtained solid for 8 hours at 60-65° C. to get the title compound. Yield: 75.0%

The obtained crystalline solid herein designated as Form-M is characterized by powder X-ray diffractogram having peaks at about 3.5, 6.9, 7.6, 9.8, 14.1, 14.4, 15.0, 15.7, 17.7, 19.3, 19.9, 20.3, 22.2, 22.9, 23.1 and 25.4±0.2 degrees two-theta as illustrated in figure-1.

Example-19

Preparation of amorphous 4-(4-(4-(4-(((3R,5R)-5-((1H-1,2,4-triazol-1-yl)methyl)-5-(2,4-difluorophenyl)tetrahydrofuran-3-yl)methoxy)phenyl)piperazin-1-yl)phenyl)-1-((2S,3R)-2-(benzyloxy)pentan-3-yl)-1H-1,2,4-triazol-5(4H)-one (Formula-21)

A solution of sodium hydroxide (9.2 g) and water (10 ml) was cooled to 25-35° C. and added dimethyl sulfoxide (350 ml), followed by 1-((2S,3S)-2-(benzyloxy)pentan-3-yl)-4-(4-(4-(4-hydroxyphenyl)piperazin-1-yl)phenyl)-1H-1,2,4-triazol-5(4H)-one (50 gms) compound of formula-20 at 25-35° C. The reaction mixture was stirred for 45 minutes at the same temperature. ((3S,5R)-5-((1H-1,2,4-triazol-1-yl)methyl)-5-(2,4-difluoro phenyl)tetrahydrofuran-3-yl)methyl 4-methylbenzenesulfonate (50 μms) compound of formula-10 was added to the above reaction mixture and heated to 45-60° C. The reaction mixture was stirred for 6 hours at the same temperature. After completion of the reaction, the reaction mixture was quenched with water and neutralized with hydrochloric acid. The reaction mixture was stirred for 1 hour at 25-35° C. Filtered the solid and washed with water. Dried the solid to get the title compound. Yield: 79 g

Example-20

Preparation of Benzylated Posaconazole: [Form-M]

Added 1-((2S,3S)-2-(benzyloxy)pentan-3-yl)-4-(4-(4-(4-hydroxyphenyl) piperazin-1-yl)phenyl)-1H-1,2,4-triazol-5 (4H)-one compound of formula-20 (35 g) to a mixture of dimethylsulfoxide (350 ml) and sodium hydroxide (3.4 g) and water (7 ml) at 25-30° C. and stirred for 45 minutes at 25-30° C. ((3S,5R)-5-((1H-1,2,4-triazol-1-yl)methyl)-5-(2,4-difluorophenyl)tetrahydrofuran-3-yl)methyl-4-methylbenzenesulfonate compound of formula-10 (31.5 g) was added to the above reaction mixture at 25-30° C. and heated the reaction mixture to 45° C. and stirred for 5 hours at the same temperature. After completion of the reaction, cooled the reaction mixture to room temperature and water was added to the reaction mixture. The reaction mixture was extracted twice with ethyl acetate. Adjusted the pH of the reaction mixture with aqueous hydrochloric acid solution. The organic layers were washed with sodium chloride solution. Distilled off the solvent under reduced pressure to get the compound as residue. Dissolved the obtained residue in isopropanol (320 ml) at 45-50° C. Filtered the solid, washed with isopropanol and dried aerially to get the title compound. Yield: 98%; Purity by HPLC: 99.5%; M.R: 117° C.-119° C.

PXRD of obtained crystalline form-M of benzylated posaconazole is depicted in figure-3.

Example-21

Preparation of Crystalline Posaconazole: [Form-S]

5N hydrochloric acid (50 ml) and 5% Pd/C (25 g) were added to benzylated posaconazole (50 g) obtained from example-20 in methanol (630 ml). The reaction was hydrogenated for 5 hours under a hydrogen gas pressure of 4-5 kg/cm$^2$ at 50° C. After completion of the reaction, the catalyst was filtered off and the catalyst is quenched with aqueous hydrochloric acid. Acetone (100 ml) was added to the filtrate and pH of the filtrate was adjusted to 7.0 using 4N sodium hydroxide. Water was added to the reaction mixture and stirred for 2 hours at 25-30° C. Filtered the separated solid and washed with water to get title compound. Yield: 30 g PXRD of the obtained crystalline form-S of posaconazole is depicted in figure-4.

Example-22

Preparation of Crystalline Form of Posaconazole: [Form-N]

Posaconazole (30 g) was dissolved in acetone (500 ml) and heated to reflux for 30 minutes. Filtered the reaction mixture through hyflow bed and added purified water (500 ml) to the reaction mixture. Stirred the reaction mixture at 30° C. for 1 hour. Filtered the precipitated solid and washed with purified water to get the title compound. Yield: 22 g. PXRD of the obtained crystalline form-N of posaconazole is depicted in figure-5.

Example-23

Preparation of Crystalline IPA Solvate Form of Posaconazole

Dissolved the posaconazole (30 g) in isopropyl alcohol (300 ml) by heating to reflux temperature. Filtered the reaction mixture and the filtrate was cooled to 25-30° C. and stirred for 2 hours at 25-30° C. Filtered the precipitated solid and washed with isopropyl alcohol. Dried the obtained solid for 8 hours at 60-65° C. to get the title compound.

Yield: 24 g.

Example-24

Preparation of Amorphous Posaconazole Compound of Formula-1

Posaconazole (100 g) and dichloromethane (500 ml) were charged into a clean and dry RBF at 25-30° C. and the resulting mixture was stirred for 15 minutes at the same temperature to get clear solution. The solution was filtered and the filtrate was slowly added to n-pentane (7500 ml) in another RBF at −30 to −20° C. The resulting mixture was stirred for 2 hrs at the same temperature. The compound obtained was filtered and washed with n-pentane and dried to get the title compound.

Yield: 95%; Particle size distribution: D(0.1): 14.95 μm; D(0.5): 59.38 μm; D(0.9): 127.80 μm.

Example-25

Preparation of Amorphous Posaconazole Compound of Formula-1

The amorphous posaconazole compound of formula-1 can be obtained by repeating the process exemplified in example-24 at a temperature of 20-33° C. to get the title compound.

Example-26

One-Pot Process for the Preparation of Amorphous Posaconazole Compound of Formula-1

5N hydrochloric acid (200 ml) and 5% Pd—C(50 g) were added to a solution of 4-(4-(4-(4-(((3R,5R)-5-((1H-1,2,4-triazol-1-yl)methyl)-5-(2,4-difluorophenyl)tetrahydro furan-3-yl)methoxy)phenyl)piperazin-1-yl)phenyl)-1-((2S,3S)-2-(benzyloxy)pentan-3-yl)-1H-1,2,4-triazol-5(4H)-one (100 g) in methanol (850 ml) in an autoclave. The reaction mixture was hydrogenated for 5 hours under a hydrogen gas pressure of 4 kg/cm$^2$ at 50° C. After completion of the reaction, the reaction mixture was filtered off and washed with methanol. pH of the filtrate was adjusted to 7.0 with aqueous sodium hydroxide solution. Water was added to the reaction mixture and stirred for 1 hour at 25-35° C. Filtered the precipitated solid and washed with purified water. Acetone (1200 ml) was added to the obtained solid and heated to 55-60° C. Stirred the reaction mixture for 30 minutes and filtered on hyflow bed and washed with acetone. 1300 ml of water was slowly added to the filtrate at 30-35° C. Stirred the reaction mixture for 60 minutes at 30-35° C. and filtered the precipitated solid and washed the solid with water. The obtained solid was dissolved in 1000 ml of isopropyl alcohol at 60-65° C. Cooled the reaction mixture to 30-35° C. and stirred for 2 hours at 30-35° C. The precipitated solid was filtered and washed with isopropyl alcohol. The obtained solid was dissolved in 280 ml of dichloromethane. The obtained solution was filtered and the filtrate was added to 4200 ml of n-heptane at 25-30° C. The reaction mixture was stirred for 2 hours at 25-30° C., filtered the obtained solid and washed with n-heptane. Dried the obtained solid to get amorphous compound of formula-1.

Yield: 52 g.

Example-27

One-Pot Process for the Preparation of Amorphous Posaconazole Compound of Formula-1

5N hydrochloric acid (200 ml) and 5% Pd—C(50 g) were added to a solution of 4-(4-(4-(4-(((3R,5R)-5-((1H-1,2,4-triazol-1-yl)methyl)-5-(2,4-difluorophenyl)tetrahydro furan-3-yl) methoxy)phenyl)piperazin-1-yl)phenyl)-1-((2S,3S)-2-(benzyloxy)pentan-3-yl)-1H-1,2,4-triazol-5(4H)-one (100 g) in methanol (850 ml) in an autoclave. The reaction mixture was hydrogenated for 5 hours under a hydrogen gas pressure of 4 kg/cm² at 50° C. After completion of the reaction, the reaction mixture was filtered off and washed with methanol. pH of the filtrate was adjusted to 7.0 with aqueous sodium hydroxide solution. Water was added to the reaction mixture and stirred for 1 hour at 25-35° C. Filtered the precipitated solid and washed with purified water. Acetone (1200 ml) was added to the obtained solid and heated to 55-60° C. Stirred the reaction mixture for 30 minutes and filtered on hyflow bed and washed with acetone. 1300 ml of water was slowly added to the filtrate at 30-35° C. Stirred the reaction mixture for 60 minutes at 30-35° C. and filtered the precipitated solid and washed the solid with water. The obtained solid was dissolved in 300 ml of dichloromethane. The obtained solution was filtered and the filtrate was added to 4500 ml of n-heptane at 25-30° C. The reaction mixture was stirred for 2 hours at 25-30° C., filtered the obtained solid and washed with n-heptane. Dried the obtained solid to get amorphous compound of formula-1.
Yield: 55 g.

Example-28

One-Pot Process for the Preparation of Amorphous Posaconazole Compound of Formula-1

5N hydrochloric acid (100 ml) and 5% Pd—C(25 g) were added to a solution of 4-(4-(4-(4-(((3R,5R)-5-((1H-1,2,4-triazol-1-yl)methyl)-5-(2,4-difluorophenyl)tetrahydro furan-3-yl)methoxy)phenyl)piperazin-1-yl)phenyl)-1-((2S,3S)-2-(benzyloxy)pentan-3-yl)-1H-1,2,4-triazol-5(4H)-one (50 g) in methanol (500 ml) in an autoclave. The reaction mixture was hydrogenated for 5 hours under a hydrogen gas pressure of 4 kg/cm² at 50° C. After completion of the reaction, the catalyst was filtered off and washed with methanol and the Pd—C was quenched with aqueous hydrochloric acid solution. pH of the filtrate was adjusted to 7.0 with aqueous sodium hydroxide solution. Water was added to the reaction mixture and stirred for 1 hour at 25-35° C. Filtered the precipitated solid and washed with purified water. The obtained solid was converted in to amorphous posaconazole compound of formula-1 by repeating the process disclosed in above example-24 & 25.
Yield: 95%.

Example-29

Preparation of Crystalline Form-I of Posaconazole Compound of Formula-1

Posaconazole (100 g) and dichloromethane (500 ml) were charged into a clean and dry RBF at 25-30° C. and the resulting mixture was stirred for 15 minutes at the same temperature. The reaction mixture was filtered and 80% of the solvent from the filtrate was distilled off under reduced pressure and co-distilled with isopropanol. The isopropanol (2000 ml) was added to the obtained residue. Heated the reaction mixture to 70-75° C. and stirred for 15 minutes at the same temperature. The reaction mixture was cooled to 25-30° C. and stirred for 2 hours at the same temperature. Filtered the precipitated solid and washed with isopropanol then dried to get crystalline Form-I of Posaconazole.
M.R: 168-171° C.; Yield: 96%; Particle size distribution: D(0.1): 5.06 µm; D(0.5): 12.69 µm; D(0.9): 28.54 µm.

The PXRD of the obtained compound matches with prior-art crystalline Form-I of Posaconazole.

Example-30

Preparation of Amorphous Posaconazole from Crystalline Form-I of Posaconazole

Crystalline form-I of Posaconazole (100 g) and dichloromethane (500 ml) were charged into a clean and dry RBF at 25-30° C. and the resulting mixture was stirred to get clear solution. The solution was filtered and the filtrate was slowly added to n-pentane (7500 ml) in another RBF at 25 to 30° C. The resulting mixture was stirred for 2 hrs at the same temperature. The precipitated solid was filtered and washed with n-pentane and dried to get the title compound.
Yield: 95%.

Example-31

Preparation of Amorphous Posaconazole from Crystalline Form-I of Posaconazole

The amorphous posaconazole compound of formula-1 can be obtained by repeating the process exemplified in example-30 at a temperature of −30 to −20° C. to get the title compound.

Example-32

Preparation of Form-I of Posaconazole from Crystalline Form-III of Posaconazole

Crystalline form-III of Posaconazole (100 g) and isopropanol (2000 ml) were charged into a clean and dry RBF at 25-30° C. The reaction mixture was heated to 70-75° C. to get the clear dissolution. The reaction mixture was slowly cooled to 25-30° C. and stirred for 2 hours at the same temperature. Filtered the precipitated solid washed with isopropanol and then dried to get crystalline Form-I of Posaconazole.
M.R: 168-171° C.; Yield: 96%;
Particle size distribution: D(0.1): 2.80 µm; D(0.5): 6.22 µm; D(0.9): 16.37 µm.
The PXRD of the obtained compound matches with prior-art crystalline Form-I of Posaconazole.

Example-33

Preparation of Amorphous Posaconazole from Crystalline Form-III of Posaconazole

Crystalline form-III of Posaconazole (100 g) and dichloromethane (500 ml) were charged into a clean and dry RBF and the resulting mixture was stirred to get clear solution. The solution was filtered and the filtrate was slowly added to n-pentane (7500 ml) in another RBF at −30 to −20° C. The resulting mixture was stirred for 2 hrs at the same temperature. The compound obtained was filtered and washed with n-pentane. Suck dried the product for 30 min followed by dried aerially for 2 hrs. Finally the product was dried at 50-55° C. to get the title compound.
Yield: 95%.

The crystalline form-III of the posaconazole used as a starting material in example-32 & 33 can be prepared from the process known in the art or from the process disclosed in U.S. Pat. No. 6,958,337 hereinafter incorporated as a reference.

We claim:

1. A process for the preparation of triazole derivative compound of Formula-1

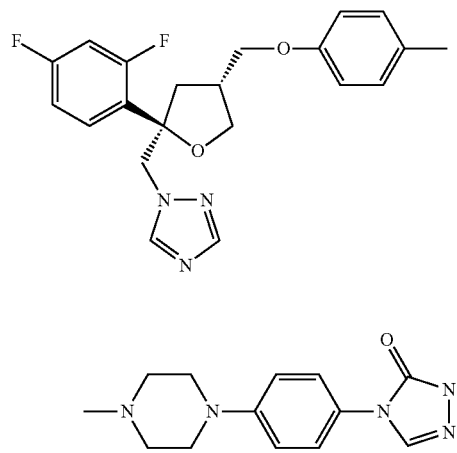

Formula 1 comprising:

a) reacting a compound of Formula-16

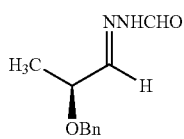

Formula-16 with ethyl magnesium halide in the presence of bis(trimethylsilyl)acetamide in a solvent to provide a compound of Formula-17,

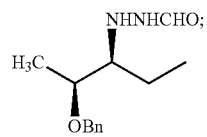

Formula-17 b) reacting the compound of Formula-17 in-situ with a compound of Formula-19

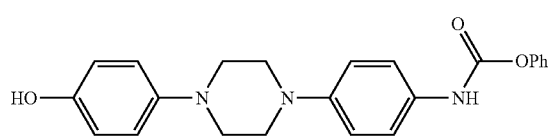

Formula-19 in the presence of a base in a solvent to provide a compound of Formula-20,

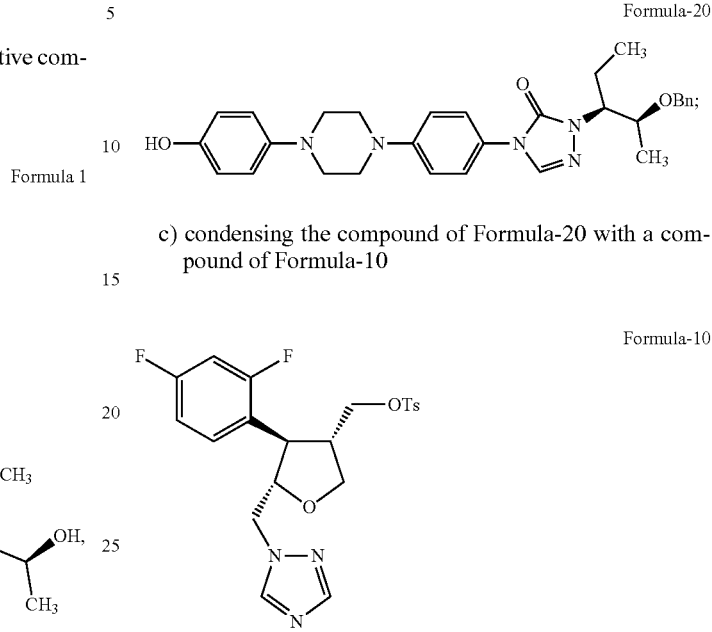

Formula-20 c) condensing the compound of Formula-20 with a compound of Formula-10

Formula-10 in the presence of a base in a polar aprotic solvent to provide a compound of Formula-21,

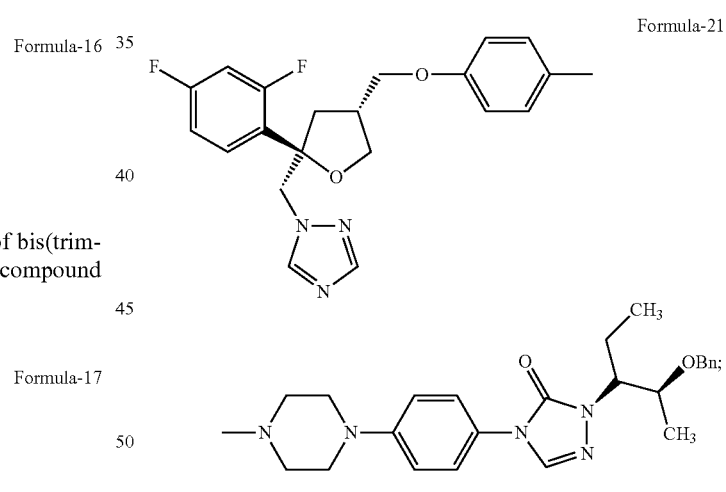

Formula-21 d) debenzylating the compound of Formula-21 with Pd/C under hydrogen pressure in the presence of mineral acid in an alcoholic solvent to provide the compound of Formula-1; and e) optionally, purifying the compound of Formula-1 obtained in step-(d) from a solvent to provide pure compound of Formula-1.

2. The process according to claim 1, wherein:

in step (a), the solvent is methyl tertiary butyl ether, tetrahydrofuran, diethyl ether, methyl tert-butyl ether or dioxane;

in step (b), the base is an organic base and the solvent is ether solvent selected from tetrahydrofuran, dioxane, tertiarybutylmethyl ether or diethyl ether;

in step (c), the base is an inorganic base and the polar aprotic solvent is selected from dimethylformamide, dimethylacetamide or dimethylsulfoxide;
in step (d), the mineral acid is hydrochloric acid, hydroiodic acid or sulfuric acid and the alcoholic solvent is methanol, ethanol, isopropanol or butanol; and
in step (e), the solvent is an alcoholic solvent.

3. The process according to claim 1, wherein the process for the preparation of the compound of Formula-10 comprises:

i) hydrolyzing a compound of Formula-6

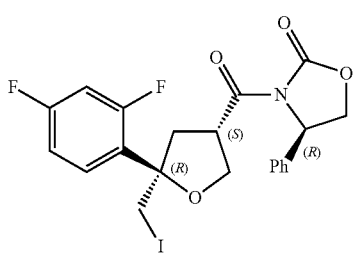

Formula-6 in presence of a base and hydrogen peroxide in a solvent to provide a compound of Formula-7,

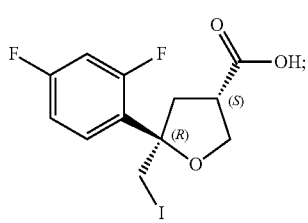

Formula-7 ii) reducing the compound of Formula-7 with a reducing agent in a solvent to provide a compound of Formula-8,

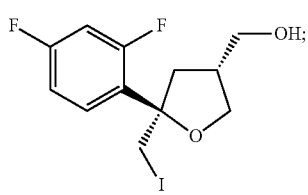

Formula-8 iii) reacting the compound of Formula-8 with 1,2,4-triazole in presence of a base in a solvent to provide a compound of Formula-9,

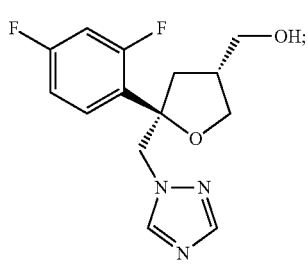

Formula-9 iv) reacting the compound of Formula-9 in-situ with tosyl chloride in presence of a base in a solvent to provide the compound of Formula-10.

4. The process according to claim 3, wherein:

in step (i), the base is an inorganic base; and the solvent is selected from ether solvents, ester solvents or ketone solvents;

in step (ii), the reducing agent is selected from DIBAL-H, lithium aluminiumhydride, sodiumborohydride, lithiumborohydride, $NaBH_3CN$, sodiumborohydride/$BF_3$-etherate, vitride, sodium borohydride/aluminium chloride or borane/aluminiumchloride, sodiumborohydride/iodine or 9-BBN; and the solvent is selected from ether solvents, ester solvents or ketone solvents;

in step (iii), the base is an organic base selected from triethylamine, tributyl amine, pyridine, 4-dimethylaminopyridine, N-methylmorpholine or diisopropylethyl amine, or an inorganic base selected from alkali metal carbonates, alkali metal hydroxide, alkali metal bicarbonates, or alkali metal alkoxides; and the solvent is selected from polar aprotic solvents, chloro solvents, ester solvents, or ketone solvents; and in step (iv), the base is selected from an organic base selected from triethylamine, tributyl amine, pyridine, 4-dimethylaminopyridine, N-methylmorpholine or diisopropylethyl amine; and the solvent is selected from chloro solvents, alcoholic solvents, or hydrocarbon solvents.

5. The process according to claim 3, wherein the process for the preparation of the compound of Formula-7 comprises:

A) reacting a compound of Formula-2

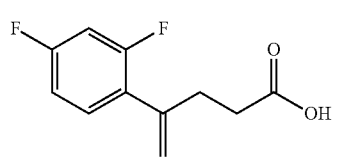

Formula-2 with a compound of Formula-3

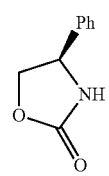

Formula-3 in presence of an activating agent and a base in a solvent to provide a compound of Formula-4,

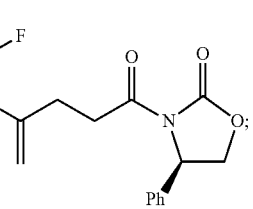

Formula-4

B) hydroxymethylating the compound of Formula-4 with 1,3,5-trioxane in presence of a base and a catalyst in a solvent to provide a compound of Formula-5, Formula-5

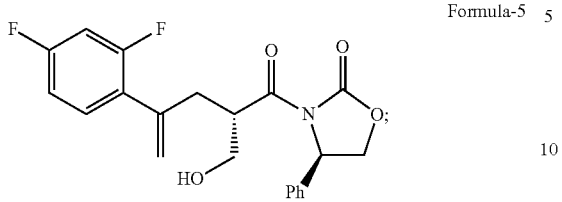

C) cyclizing the compound of Formula-5 in-situ in presence of iodine and a base in a solvent to provide a compound of Formula-6, Formula-6

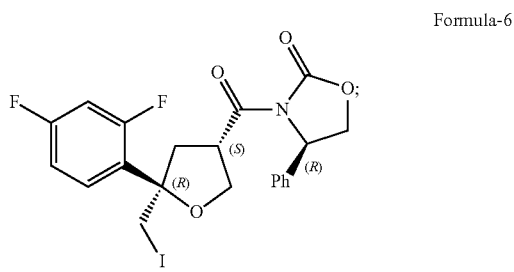

D) hydrolyzing the compound of Formula-6 in presence of an aqueous base and hydrogen peroxide in a solvent to provide the compound of Formula-7.

6. The process according to claim 5, wherein:
in step (A), the activating agent is selected from thionyl chloride, oxalyl chloride, pivaloyl chloride, carbonylditriazole, oxalylditriazole, $POCl_3$, $PCl_3$, $PCl_5$ or $SO_2Cl_2$; the organic base is selected from triethylamine, tributyl amine, pyridine, 4-dimethylaminopyridine, N-methylmorpholine or diisopropylethyl amine and the solvent is selected from chloro solvents, ester solvents, ketone solvents, polar aprotic solvents or alcoholic solvents or mixture thereof;
in step (B), the base is an organic base; the catalyst is titanium tetrachloride; and the solvent is selected from chloro solvent, ketone solvents, ester solvents, ether solvents or alcoholic solvents;
in step (C), the base is selected from alkali metal hydroxides, alkali metal alkoxides, alkali metal carbonates, or alkali metal bicarbonates; and the solvent is selected from ether solvents, chloro solvents, alcoholic solvents or ester solvents or a mixture thereof; and
in step (D), the base is an organic base or an inorganic base; and the solvent is selected from ether solvents, ester solvents, ketone solvents or hydrocarbon solvents.

7. The process according to claim 5, wherein the amount of hydrogen peroxide used in step (D) is between 1.0-2.0 moles per one mole of compound of Formula-6.

8. The process according to claim 1, wherein the process for the preparation of the compound of Formula-19 comprises reacting a compound of Formula-18

Formula-18

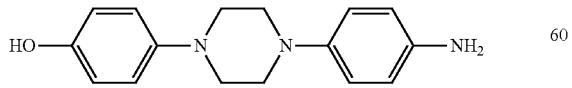

with phenylchloroformate in the absence of a base in a solvent selected from polar aprotic solvents, chloro solvents, ester solvents, ketone solvents, alcoholic solvents or ether solvents to provide the compound of Formula-19.

9. The process according to claim 1, wherein step (c) further comprises:
i) condensing the compound of Formula-20 with the compound of Formula-10 in the presence of an aqueous base selected from alkali metal hydroxides, alkali metal alkoxides, alkali metal carbonates, or alkali metal bicarbonates in a solvent selected from polar aprotic solvents, chloro solvents, ester solvents, or ether solvents to provide the compound of Formula-21;
ii) quenching the reaction mixture with water; and
iii) neutralizing the reaction mixture with an acid to provide amorphous compound of Formula-21.

10. The process according to claim 1, wherein the process for the preparation of the compound of Formula-16 comprises:
i) reacting racemic methyl lactate with benzyl chloride in the presence of an alkali metal alkoxide in a solvent selected from polar aprotic solvents, ester solvents, chloro solvents or alcoholic solvents to provide a compound of Formula-12

Formula-12

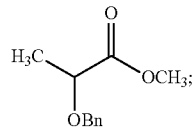

ii) hydrolyzing the compound of Formula-12 in-situ with an alkali metal hydroxide in a solvent selected from hydrocarbon solvents, ester solvents, or alcoholic solvents to provide a compound of Formula-13

Formula-13

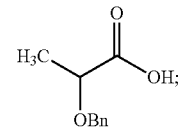

iii) resolving the compound of Formula-13 in-situ with (S)-1-phenylethanamine in a solvent selected from hydrocarbon solvents, chloro solvents or ester solvents to provide a compound of Formula-13a Formula-13a

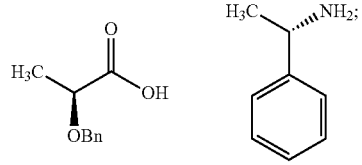

iv) reacting the compound of Formula-13a with methanol in presence of thionyl chloride in a polar aprotic solvent to provide a compound of Formula-14

Formula-14

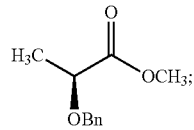

v) reducing the compound of Formula-14 with DIBAL-H in toluene to provide a compound of Formula-15

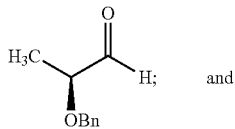

Formula-15 and vi) reacting the compound of Formula-15 in-situ with formyl hydrazine in methanol to provide the compound of Formula-16.

11. The process according to claim 1, wherein the compound of Formula-1 is in the form of:
   a) isopropanol solvate compound of Formula-1 characterized by its powder X-ray diffractogram having peaks at about 3.5, 6.9, 7.6, 9.8, 14.1, 14.4, 15.0, 15.7, 17.7, 19.3, 19.9, 20.3, 22.2, 22.9, 23.1 and 25.4±0.2 degrees of two-theta;
   b) crystalline form-S compound of Formula-1 characterized by its powder X-ray diffractogram having peaks at about 7.19, 7.95, 10.20, 13.91, 15.38, 16.05, 16.69, 17.32, 17. 77, 18.95, 19.29, 19.83, 20.20, 21.32, 21.67, 23.44, 24.70, 25.93, 26.64 and 27.79.±0.2 degrees of two theta; or
   c) crystalline form-N compound of Formula-1 characterized by its powder X-ray diffractogram having peaks at about 7.92, 10.17, 10.86, 11.26, 12.98, 13.86, 17.72, 18.66, 22.62, 24.65, 25.84 and 28.52±0.2 degrees of two theta.

12. The process according to claim 11, wherein the compound of Formula-1 is in the form of the isopropanol solvate compound of Formula-1 and is prepared by a process comprising:
   i) dissolving the compound of Formula-1 in isopropanol by heating to reflux temperature;
   ii) filtering the reaction mixture;
   iii) cooling the reaction mixture;
   iv) stirring the reaction mixture;
   v) filtering the solid and washing with isopropanol; and
   vi) drying the solid to get crystalline isopropanol solvate of compound of Formula-1.

13. The process according to claim 11, wherein the compound of Formula-1 is in the form of crystalline form-S compound of Formula-1 and is prepared by a process comprising:
   i) debenzylating the compound of Formula-21 with Pd/C under hydrogen pressure in the presence of mineral acid in an alcoholic solvent to provide the compound of Formula-1 in accordance with step (d);
   ii) filtering the reaction mixture;
   iii) adding an organic solvent to the reaction mixture;
   iv) cooling the reaction mixture to 10 to 15° C.;
   v) adjusting pH of the reaction mixture;
   vi) adding purified water to the reaction mixture;
   vii) stirring the reaction mixture; and
   viii) filtering the solid and washing with purified water to get crystalline form-S of compound of Formula-1.

14. The process according to claim 13, wherein:
   in step (i), the mineral acid is selected from hydrochloric acid, hydrobromic acid, hydroiodic acid or sulfuric acid and the alcoholic solvent is methanol, ethanol, or isopropanol; and
   in step (iii), the organic solvent is a ketone solvent.

15. The process according to claim 11, wherein the compound of Formula-1 is in the form of crystalline form-N compound of Formula-1 and is prepared by a process comprising:
   i) dissolving the compound of Formula-1 in acetone;
   ii) heating the reaction mixture to reflux;
   iii) filtering the reaction mixture;
   iv) adding purified water to the filtrate;
   v) stirring the reaction mixture; and
   vi) filtering the solid and washing with purified water to get crystalline form-N of compound of Formula-1.

16. The process according to claim 1, wherein the compound of Formula-21 is in amorphous form.

17. The process according to claim 1, wherein the compound of Formula-21 is characterized by its powder X-ray diffractogram having peaks at about 3.90, 5.86, 7.82, 9.82, 11.79, 12.59, 13.38, 13.74, 16.24, 16.95, 17.83, 18.90, 20.09, 21.49, 22.89, 24.93, 26.53, 27.56, 28.73, 29.88 and 34.20±0.2 degrees of two theta.

18. The process according to claim 1, further comprising:
   i) dissolving the compound of Formula-1 in a solvent selected from chloro solvents, ketone solvents, ester solvents, ether solvents, or alcoholic solvents;
   ii) filtering the reaction mixture;
   iii) adding filtrate to a non-polar solvent;
   iv) stirring the reaction mixture; and
   v) filtering the solid and then drying to get amorphous form of compound of Formula-1.

19. The process according to claim 18, comprising:
   i) dissolving the compound of Formula-1 in dichloromethane;
   ii) filtering the reaction mixture;
   iii) adding filtrate to n-pentane;
   iv) stirring the reaction mixture; and
   v) filtering the solid and then drying to get amorphous form of compound of Formula-1.

20. The process according to claim 1, further comprising:
   i) debenzylating the compound of Formula-21 with Pd/C under hydrogen pressure in presence of hydrochloric acid in methanol;
   ii) filtering the reaction mixture and adding acetone to the filtrate;
   iii) cooling the reaction mixture and adjusting the pH of the reaction mixture;
   iv) adding water to the reaction mixture;
   v) filtering the precipitated solid;
   vi) adding acetone to the solid obtained in step (v) and heating the reaction mixture;
   vii) filtering the reaction mixture;
   viii) adding water to the filtrate and stirring the reaction mixture;
   ix) filtering the precipitated solid;
   x) optionally, purifying the solid obtained in step (ix);
   xi) adding dichloromethane to the solid;
   xii) slowly adding the mixture obtained in step (xi) to n-pentane;
   xiii) stirring the reaction mixture; and
   xiv) filtering the solid and then drying to get amorphous form of compound of Formula-1.

* * * * *